United States Patent
Coe et al.

(10) Patent No.: US 8,233,995 B2
(45) Date of Patent: Jul. 31, 2012

(54) SYSTEM AND METHOD OF ALIGNING AN IMPLANTABLE ANTENNA

(75) Inventors: Jonathan A. Coe, Cincinnati, OH (US); Mark S. Ortiz, Milford, OH (US); Michael J. Stokes, Cincinnati, OH (US); Christine Hsin Yi Chen, Cincinnati, OH (US); Juan S. Ezolino, Weston, FL (US); Kevin D. Felder, Cincinnati, OH (US); Eric W. Thompson, Pleasant Plain, OH (US); David C. Yates, West Chester, OH (US); David N. Plescia, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1182 days.

(21) Appl. No.: 12/043,230

(22) Filed: Mar. 6, 2008

(65) Prior Publication Data
US 2009/0228072 A1    Sep. 10, 2009

(51) Int. Cl.
*A61N 1/372*    (2006.01)
*A61N 1/375*    (2006.01)
*A61N 1/02*    (2006.01)
(52) U.S. Cl. .................. 607/133; 607/40; 607/60
(58) Field of Classification Search .......... 607/40, 607/60, 133
See application file for complete search history.

(56) References Cited

U.S. PATENT DOCUMENTS

| | | |
|---|---|---|
| RE3,036 E | 7/1868 | Shunk |
| RE3,037 E | 7/1868 | Tucker |
| RE3,115 E | 9/1868 | Lewis |
| RE3,187 E | 11/1868 | Winchester |
| RE3,322 E | 3/1869 | Murch |
| 236,373 A | 1/1881 | Spilman |
| 322,388 A | 7/1885 | Lord |
| 400,401 A | 3/1889 | Gutzkow |
| D23,637 S | 9/1894 | Casad et al. |
| D24,900 S | 11/1895 | Clemecet |

(Continued)

FOREIGN PATENT DOCUMENTS

CA    1059035    7/1979

(Continued)

OTHER PUBLICATIONS

"Application Specific Integrated Circuits (ASICs)", Honeywell product information from website http://www.honeywell.com/sites/portal?smap=aerospace&page=Radiation-Hardened-Electronics3&theme=T18&catID=CEO6BEF88-65F8-6A1E-4ED1-6A1EC1B7AE7A&id=HA0E380D3-C27B-9EBF-AAC8-9FAF8851256D&sel=1&sel4=1; 1 page.

(Continued)

*Primary Examiner* — Tammie K Heller
(74) *Attorney, Agent, or Firm* — Nutter McClennen & Fish LLP

(57) ABSTRACT

An implantable restriction system having an antenna capable of being readily and predictably movable to achieve a desired orientation that is effective to communicate with an external device is provided. The antenna can be movably coupled to a housing such that the antenna can float and/or move freely with respect to the housing. The housing can be part of a gimbal element or another component of the system. The antenna can include a weight or a magnetic element to help it achieve the desired orientation. Methods for transcutaneously communicating with an implantable restriction device are also provided.

17 Claims, 11 Drawing Sheets

U.S. PATENT DOCUMENTS

| | | | |
|---|---|---|---|
| D25,318 S | 3/1896 | Perky | |
| D27,151 S | 6/1897 | Moulten | |
| D29,715 S | 11/1898 | Wheeler | |
| D29,745 S | 11/1898 | Bunker | |
| D29,885 S | 12/1898 | Gillespie et al. | |
| D30,690 S | 5/1899 | Schwedtmann | |
| D30,966 S | 6/1899 | Howe | |
| D31,230 S | 7/1899 | Hogan | |
| 689,758 A | 12/1901 | Shaw | |
| 724,913 A | 4/1903 | Montgomery | |
| 899,477 A | 9/1908 | Williams | |
| 926,197 A | 6/1909 | Kim | |
| 953,875 A | 4/1910 | Waring | |
| 991,192 A | 5/1911 | Batttenfeld | |
| 1,087,988 A | 2/1914 | Sheldon | |
| 1,210,701 A | 1/1917 | Ryden | |
| 1,219,296 A | 3/1917 | Hahn | |
| 1,224,355 A | 5/1917 | Brown | |
| 1,263,914 A | 4/1918 | Martin | |
| 1,310,290 A | 7/1919 | Piechowicz | |
| 1,384,873 A | 7/1921 | Strickland | |
| 1,421,507 A | 7/1922 | Lindberg | |
| 1,551,525 A | 8/1925 | Hamer | |
| 1,560,973 A | 11/1925 | Cheron | |
| 1,620,633 A | 3/1927 | Colvin | |
| 1,623,403 A | 4/1927 | Friel | |
| 1,689,085 A | 10/1928 | Russell et al. | |
| 1,764,071 A | 6/1930 | Foulke | |
| 1,782,704 A | 11/1930 | Woodruff | |
| 1,807,107 A | 5/1931 | Sternberch | |
| 1,865,446 A | 7/1932 | Sears | |
| 1,882,338 A | 10/1932 | Reed et al. | |
| 1,924,781 A | 8/1933 | Gaiser | |
| 2,027,875 A | 1/1936 | Odend'hal | |
| 2,063,430 A | 12/1936 | Graser | |
| 2,099,160 A | 11/1937 | Charch | |
| 2,105,127 A | 1/1938 | Petrone | |
| 2,106,192 A | 1/1938 | Saville | |
| 2,143,429 A | 1/1939 | Auble | |
| 2,166,603 A | 7/1939 | Menzer | |
| 2,168,427 A | 8/1939 | McConkey | |
| 2,174,525 A | 10/1939 | Padernal | |
| 2,177,564 A | 10/1939 | Havill | |
| 2,178,463 A | 10/1939 | Bahnson | |
| 2,180,599 A | 11/1939 | Menasco | |
| 2,203,460 A | 6/1940 | Fieber | |
| 2,206,038 A | 7/1940 | Lang Ford | |
| 2,216,374 A | 10/1940 | Martin | |
| 2,223,699 A | 12/1940 | Norgren | |
| 2,225,145 A | 12/1940 | Baumbach | |
| 2,225,880 A | 12/1940 | Montelius | |
| 2,261,060 A | 10/1941 | Giesler | |
| 2,261,355 A | 11/1941 | Flynn | |
| 2,295,539 A | 9/1942 | Beach | |
| 2,303,108 A | 11/1942 | Blackburn | |
| 2,303,502 A | 12/1942 | Rous | |
| 2,318,819 A | 5/1943 | Verson | |
| 2,327,407 A | 8/1943 | Edyvean | |
| 2,327,615 A | 8/1943 | Ankarlo | |
| 2,354,571 A | 7/1944 | Blain | |
| 2,426,392 A | 8/1947 | Fennema | |
| 2,426,817 A | 9/1947 | Charlton et al. | |
| 2,440,260 A | 4/1948 | Gall | |
| 2,442,573 A | 6/1948 | Stafford | |
| 2,453,217 A | 11/1948 | Gregg et al. | |
| 2,455,859 A | 12/1948 | Foley | |
| 2,477,922 A | 8/1949 | Emery et al. | |
| 2,478,876 A | 8/1949 | Nelson | |
| 2,482,392 A | 9/1949 | Whitaker | |
| 2,494,881 A | 1/1950 | Kost | |
| 2,509,210 A | 5/1950 | Clark | |
| 2,509,673 A | 5/1950 | Church | |
| 2,511,765 A | 6/1950 | Bradbury | |
| 2,520,056 A | 8/1950 | Pozun | |
| 2,521,976 A | 9/1950 | Hays | |
| 2,533,924 A | 12/1950 | Foley | |
| 2,538,259 A | 1/1951 | Merriman | |
| 2,581,479 A | 1/1952 | Grashman | |
| 2,600,324 A | 6/1952 | Rappaport | |
| 2,606,003 A | 8/1952 | McNeill | |
| 2,615,940 A | 10/1952 | Williams | |
| 2,632,447 A | 3/1953 | Dobes | |
| 2,639,342 A | 5/1953 | Cope | |
| 2,640,119 A | 5/1953 | Bradford, Jr. | |
| 2,641,742 A | 6/1953 | Wolfe | |
| 2,651,304 A | 9/1953 | Browner | |
| 2,665,577 A | 1/1954 | Sanowskis | |
| 2,673,999 A | 4/1954 | Shey | |
| 2,676,609 A | 4/1954 | Pfarrer | |
| 2,684,118 A | 7/1954 | Osmun | |
| 2,689,611 A | 9/1954 | Martinson | |
| 2,697,435 A | 12/1954 | Ray | |
| 2,723,323 A | 11/1955 | Niemi | |
| 2,734,992 A | 2/1956 | Elliot et al. | |
| 2,740,007 A | 3/1956 | Amelang | |
| 2,740,853 A | 4/1956 | Hatman, Jr. | |
| 2,742,323 A | 4/1956 | Shey | |
| 2,747,332 A | 5/1956 | Morehouse | |
| 2,753,876 A | 7/1956 | Kurt | |
| 2,756,883 A | 7/1956 | Schreck | |
| 2,756,983 A | 7/1956 | Furcini | |
| 2,761,603 A | 9/1956 | Fairchild | |
| 2,773,312 A | 12/1956 | Peck | |
| 2,783,728 A | 3/1957 | Hoffmann | |
| 2,787,875 A | 4/1957 | Johnson | |
| 2,793,379 A | 5/1957 | Moore | |
| 2,795,460 A | 6/1957 | Bletcher | |
| 2,804,514 A | 8/1957 | Peters | |
| 2,822,113 A | 2/1958 | Joiner, Jr. | |
| 2,831,478 A | 4/1958 | Uddenberg et al. | |
| 2,864,393 A | 12/1958 | Drake | |
| 2,865,541 A | 12/1958 | Hicks | |
| 2,870,024 A | 1/1959 | McK. Martin | |
| 2,883,995 A | 4/1959 | Bialous et al. | |
| 2,886,355 A | 5/1959 | Wurzel | |
| 2,895,215 A | 7/1959 | Neher et al. | |
| 2,899,493 A | 8/1959 | Levine | |
| 2,902,861 A | 9/1959 | Frost et al. | |
| 2,923,531 A | 2/1960 | Bauer et al. | |
| 2,924,263 A | 2/1960 | Landis | |
| 2,924,432 A | 2/1960 | Arps et al. | |
| 2,930,170 A | 3/1960 | Holsman et al. | |
| 2,938,592 A | 5/1960 | Charske et al. | |
| 2,941,338 A | 6/1960 | Santschi | |
| 2,943,682 A | 7/1960 | Ingram, Jr. et al. | |
| 2,958,781 A | 11/1960 | Marchal et al. | |
| 2,961,479 A | 11/1960 | Bertling | |
| 2,976,355 A | 3/1961 | Levine | |
| 2,976,686 A | 3/1961 | Stelzer | |
| 2,977,876 A | 4/1961 | Meyers | |
| 2,986,715 A | 5/1961 | Church at al. | |
| 2,989,019 A | 6/1961 | Van Sciver, II | |
| 3,010,692 A | 11/1961 | Jentoft | |
| 3,013,234 A | 12/1961 | Bourns | |
| 3,018,791 A | 1/1962 | Knox | |
| 3,034,356 A | 5/1962 | Bieganski | |
| 3,040,800 A | 6/1962 | Hartley | |
| 3,054,618 A | 9/1962 | Abrams at al. | |
| 3,060,262 A | 10/1962 | Hoer | |
| 3,070,373 A | 12/1962 | Mathews at al. | |
| 3,082,414 A | 3/1963 | Papaminas | |
| 3,085,577 A | 4/1963 | Berman et al. | |
| 3,096,410 A | 7/1963 | Anderson | |
| 3,099,262 A | 7/1963 | Bigliano | |
| 3,125,028 A | 3/1964 | Rohde | |
| 3,126,029 A | 3/1964 | Englesson | |
| 3,129,072 A | 4/1964 | Cook et al. | |
| 3,135,914 A | 6/1964 | Callan et al. | |
| 3,144,017 A | 8/1964 | Muth | |
| 3,151,258 A | 9/1964 | Sonderegger et al. | |
| 3,153,460 A | 10/1964 | Raskin | |
| 3,161,051 A | 12/1964 | Perry, Jr. | |
| 3,167,044 A | 1/1965 | Henrickson | |
| 3,171,549 A | 3/1965 | Orloff | |
| 3,172,700 A | 3/1965 | Haas | |
| 3,173,269 A | 3/1965 | Imbertson | |
| 3,182,494 A | 5/1965 | Beatty et al. | |

| | | | | | |
|---|---|---|---|---|---|
| 3,187,181 A | 6/1965 | Keller | 3,482,449 A | 12/1969 | Werner |
| 3,187,745 A | 6/1965 | Baum et al. | 3,482,816 A | 12/1969 | Arnold |
| 3,190,388 A | 6/1965 | Moser et al. | 3,487,959 A | 1/1970 | Pearne et al. |
| 3,205,547 A | 9/1965 | Riekse | 3,491,842 A | 1/1970 | Delacour et al. |
| 3,208,255 A | 9/1965 | Burk | 3,492,638 A | 1/1970 | Lane |
| 3,209,570 A | 10/1965 | Hills | 3,502,829 A | 3/1970 | Reynolds |
| 3,221,468 A | 12/1965 | Casey | 3,503,116 A | 3/1970 | Strack |
| 3,228,703 A | 1/1966 | Wilson | 3,504,664 A | 4/1970 | Haddad |
| 3,229,684 A | 1/1966 | Nagumo et al. | 3,505,808 A | 4/1970 | Eschle |
| 3,236,088 A | 2/1966 | Moller | 3,509,754 A | 5/1970 | Massingill et al. |
| 3,238,624 A | 3/1966 | McCabe | 3,512,517 A | 5/1970 | Kadish et al. |
| 3,240,510 A | 3/1966 | Spouge | 3,514,919 A | 6/1970 | Ashton et al. |
| 3,245,642 A | 4/1966 | Dicke | 3,516,220 A | 6/1970 | Buford et al. |
| 3,255,568 A | 6/1966 | Martin et al. | 3,517,553 A | 6/1970 | Williams et al. |
| 3,260,091 A | 7/1966 | Shaw, Jr. | 3,527,226 A | 9/1970 | Hakin et al. |
| 3,265,822 A | 8/1966 | Moulten | 3,529,908 A | 9/1970 | Smith |
| 3,266,487 A | 8/1966 | Watkins et al. | 3,530,449 A | 9/1970 | Anderson |
| 3,273,447 A | 9/1966 | Frank | 3,533,403 A | 10/1970 | Woodson |
| 3,283,352 A | 11/1966 | Hu | 3,534,728 A | 10/1970 | Barrows |
| 3,290,919 A | 12/1966 | Malinak et al. | 3,534,872 A | 10/1970 | Roth at al. |
| 3,292,493 A | 12/1966 | Franklin | 3,535,914 A | 10/1970 | Veith at al. |
| 3,292,888 A | 12/1966 | Fischer | 3,539,009 A | 11/1970 | Kudlaty |
| 3,294,988 A | 12/1966 | Packard | 3,543,744 A | 12/1970 | LePar |
| 3,299,603 A | 1/1967 | Shaw | 3,545,275 A | 12/1970 | Harrison at al. |
| 3,299,882 A | 1/1967 | Masino | 3,550,583 A | 12/1970 | Chiku |
| 3,301,514 A | 1/1967 | Sugaya | 3,550,847 A | 12/1970 | Scott |
| 3,302,457 A | 2/1967 | Mayes | 3,563,094 A | 2/1971 | Rieschel |
| 3,306,384 A | 2/1967 | Ross | 3,563,245 A | 2/1971 | McLean et al. |
| 3,313,314 A | 4/1967 | Burke et al. | 3,566,083 A | 2/1971 | McMillin |
| 3,316,935 A | 5/1967 | Kaiser et al. | 3,566,875 A | 3/1971 | Stoehr |
| 3,320,750 A | 5/1967 | Haise et al. | 3,568,367 A | 3/1971 | Myers |
| 3,321,035 A | 5/1967 | Tarpley | 3,568,636 A | 3/1971 | Lockwood |
| 3,332,788 A | 7/1967 | Barnby | 3,576,554 A | 4/1971 | Temps, Jr. et al. |
| 3,334,510 A | 8/1967 | Hallesy | 3,580,082 A | 5/1971 | Strack |
| 3,339,401 A | 9/1967 | Peters | 3,581,402 A | 6/1971 | London et al. |
| 3,340,868 A | 9/1967 | Darling | 3,583,387 A | 6/1971 | Garner et al. |
| 3,347,162 A | 10/1967 | Braznell | 3,587,204 A | 6/1971 | George |
| 3,350,944 A | 11/1967 | De Michele | 3,590,809 A | 7/1971 | London |
| 3,353,364 A | 11/1967 | Blanding et al. | 3,590,818 A | 7/1971 | Lemole |
| 3,353,481 A | 11/1967 | Antonucci | 3,590,992 A | 7/1971 | Soderstrom et al. |
| 3,356,334 A | 12/1967 | Scaramucci | 3,592,183 A | 7/1971 | Watkins et al. |
| 3,356,510 A | 12/1967 | Barnby | 3,594,519 A | 7/1971 | Schmidlin |
| 3,357,218 A | 12/1967 | Mitchell | 3,602,885 A | 8/1971 | Grajeda |
| 3,357,461 A | 12/1967 | Friendship | 3,610,016 A | 10/1971 | Bultman |
| 3,359,741 A | 12/1967 | Nelson | 3,610,851 A | 10/1971 | Krupski |
| 3,361,300 A | 1/1968 | Kaplan | 3,611,811 A | 10/1971 | Lissau |
| 3,364,929 A | 1/1968 | Ide et al. | 3,614,926 A | 10/1971 | Brechtel |
| 3,365,684 A | 1/1968 | Stemke | 3,614,955 A | 10/1971 | Mirowski et al. |
| 3,378,456 A | 4/1968 | Roberts | 3,619,742 A | 11/1971 | Rud, Jr. |
| 3,380,445 A | 4/1968 | Frasier | 3,623,371 A | 11/1971 | Jullien-Davin |
| 3,380,649 A | 4/1968 | Roberts | 3,624,854 A | 12/1971 | Strong |
| 3,385,022 A | 5/1968 | Anderson | 3,630,242 A | 12/1971 | Schieser et al. |
| 3,389,355 A | 6/1968 | Schroeder, Jr. | 3,631,847 A | 1/1972 | Hobbs, II |
| 3,393,612 A | 7/1968 | Gorgens et al. | 3,633,881 A | 1/1972 | Yurdin |
| 3,396,561 A | 8/1968 | Day | 3,635,061 A | 1/1972 | Rydell |
| 3,399,667 A | 9/1968 | Nishimoto et al. | 3,635,074 A | 1/1972 | Moos et al. |
| 3,400,734 A | 9/1968 | Rosenberg | 3,638,496 A | 2/1972 | King |
| 3,403,237 A | 9/1968 | Wysong | 3,644,883 A | 2/1972 | Borman et al. |
| 3,409,924 A | 11/1968 | Slama | 3,648,687 A | 3/1972 | Ramsey, III |
| 3,411,347 A | 11/1968 | Wirth et al. | 3,651,289 A | 3/1972 | Nagashima et al. |
| 3,417,476 A | 12/1968 | Martens | 3,651,405 A | 3/1972 | Whitney et al. |
| 3,420,325 A | 1/1969 | McAlister et al. | 3,653,671 A | 4/1972 | Shipes |
| 3,422,324 A | 1/1969 | Webb | 3,659,615 A | 5/1972 | Enger |
| 3,426,165 A | 2/1969 | Beaman | 3,677,685 A | 7/1972 | Aoki et al. |
| 3,438,391 A | 4/1969 | Yocum | 3,686,958 A | 8/1972 | Porter et al. |
| 3,443,608 A | 5/1969 | Copping et al. | 3,688,568 A | 9/1972 | Karper at al. |
| 3,445,335 A | 5/1969 | Gluntz | 3,701,392 A | 10/1972 | Wirth et al. |
| 3,447,281 A | 6/1969 | Bufford et al. | 3,702,677 A | 11/1972 | Heffington |
| 3,450,153 A | 6/1969 | Hildebrandt et al. | 3,703,099 A | 11/1972 | Rouse et al. |
| 3,453,546 A | 7/1969 | Fryer | 3,712,138 A | 1/1973 | Alinari et al. |
| 3,453,848 A | 7/1969 | Williamson | 3,713,124 A | 1/1973 | Durland et al. |
| 3,456,134 A | 7/1969 | Ko | 3,719,524 A | 3/1973 | Ripley at al. |
| 3,457,909 A | 7/1969 | Laird | 3,721,412 A | 3/1973 | Kindorf |
| 3,460,557 A | 8/1969 | Gallant | 3,723,247 A | 3/1973 | Leine at al. |
| 3,463,338 A | 8/1969 | Schneider | 3,724,000 A | 4/1973 | Eakman |
| 3,469,818 A | 9/1969 | Cowan | 3,727,463 A | 4/1973 | Intraub |
| 3,470,725 A | 10/1969 | Brown et al. | 3,727,616 A | 4/1973 | Lenzkes |
| 3,472,230 A | 10/1969 | Fogarty | 3,730,174 A | 5/1973 | Madison |
| 3,478,344 A | 11/1969 | Schwitzgebel et al. | 3,730,560 A | 5/1973 | Abildgaard et al. |

| | | | | | |
|---|---|---|---|---|---|
| 3,731,679 A | 5/1973 | Wilhelmson et al. | 3,908,461 A | 9/1975 | Turpen |
| 3,731,681 A | 5/1973 | Blackshear et al. | 3,908,721 A | 9/1975 | McGahey et al. |
| 3,732,731 A | 5/1973 | Fussell, Jr. | 3,910,087 A | 10/1975 | Jones |
| 3,735,040 A | 5/1973 | Punt et al. | 3,912,168 A | 10/1975 | Mullins et al. |
| 3,736,930 A | 6/1973 | Georgi | 3,912,304 A | 10/1975 | Abildgaard et al. |
| 3,738,356 A | 6/1973 | Workman | 3,918,286 A | 11/1975 | Whitehead |
| 3,740,921 A | 6/1973 | Meyer et al. | 3,918,291 A | 11/1975 | Pauly et al. |
| 3,746,111 A | 7/1973 | Berthiaume et al. | 3,920,965 A | 11/1975 | Sohrwardy et al. |
| 3,748,678 A | 7/1973 | Ballou | 3,921,682 A | 11/1975 | McGahey et al. |
| 3,749,098 A | 7/1973 | De Bennetot et al. | 3,922,951 A | 12/1975 | Linsinger et al. |
| 3,749,422 A | 7/1973 | Abildgaard et al. | 3,923,060 A | 12/1975 | Ellinwood, Jr. |
| 3,749,423 A | 7/1973 | Abildgaard et al. | 3,924,635 A | 12/1975 | Hakim et al. |
| 3,750,194 A | 8/1973 | Summers | 3,928,980 A | 12/1975 | Ganzinotti et al. |
| 3,757,770 A | 9/1973 | Brayshaw et al. | 3,929,175 A | 12/1975 | Coone |
| 3,759,095 A | 9/1973 | Short, Jr. et al. | 3,930,682 A | 1/1976 | Booth |
| 3,760,638 A | 9/1973 | Lawson et al. | 3,930,852 A | 1/1976 | Tanaka et al. |
| 3,763,960 A | 10/1973 | John et al. | 3,936,028 A | 2/1976 | Norton et al. |
| 3,765,142 A | 10/1973 | Lindquist et al. | 3,940,122 A | 2/1976 | Janzen et al. |
| 3,765,494 A | 10/1973 | Kielman, Jr. | 3,940,630 A | 2/1976 | Bergonz |
| 3,769,156 A | 10/1973 | Brecy et al. | 3,942,299 A | 3/1976 | Bory et al. |
| 3,769,830 A | 11/1973 | Porter et al. | 3,942,382 A | 3/1976 | Hok et al. |
| 3,774,243 A | 11/1973 | Ng et al. | 3,942,516 A | 3/1976 | Glynn et al. |
| 3,776,333 A | 12/1973 | Mathauser | 3,942,536 A | 3/1976 | Mirowski et al. |
| 3,778,051 A | 12/1973 | Allen et al. | 3,943,915 A | 3/1976 | Severson |
| 3,780,578 A | 12/1973 | Sellman et al. | 3,945,704 A | 3/1976 | Kraus et al. |
| 3,781,902 A | 12/1973 | Shim et al. | 3,946,613 A | 3/1976 | Silver |
| 3,783,585 A | 1/1974 | Hoyland et al. | 3,946,615 A | 3/1976 | Hluchan |
| 3,789,667 A | 2/1974 | Porter et al. | 3,946,724 A | 3/1976 | La Balme et al. |
| 3,796,095 A | 3/1974 | Fussell, Jr. | 3,948,141 A | 4/1976 | Shinjo et al. |
| 3,807,219 A | 4/1974 | Wallskog | 3,949,388 A | 4/1976 | Fuller |
| 3,811,429 A | 5/1974 | Fletcher et al. | 3,953,289 A | 4/1976 | Costes et al. |
| 3,815,722 A | 6/1974 | Sessoms | 3,954,271 A | 5/1976 | Tredway, Sr. |
| 3,818,765 A | 6/1974 | Eriksen et al. | 3,958,558 A | 5/1976 | Dunphy et al. |
| 3,820,400 A | 6/1974 | Russo | 3,961,425 A | 6/1976 | Swanson et al. |
| 3,820,795 A | 6/1974 | Taylor | 3,961,646 A | 6/1976 | Schon et al. |
| 3,823,610 A | 7/1974 | Fussell, Jr. | 3,962,895 A | 6/1976 | Rydell et al. |
| 3,825,065 A | 7/1974 | Lloyd et al. | 3,962,921 A | 6/1976 | Lips |
| 3,825,963 A | 7/1974 | Abildgaard et al. | 3,963,019 A | 6/1976 | Quandt |
| 3,825,964 A | 7/1974 | Groswith, III et al. | 3,964,485 A | 6/1976 | Neumeier |
| 3,828,672 A | 8/1974 | Gazzola et al. | 3,964,770 A | 6/1976 | Abildgaard et al. |
| 3,828,766 A | 8/1974 | Krasnow | 3,967,737 A | 7/1976 | Peralta et al. |
| 3,831,588 A | 8/1974 | Rindner | 3,968,473 A | 7/1976 | Patton et al. |
| 3,831,942 A | 8/1974 | Del Mar | 3,968,694 A | 7/1976 | Clark |
| 3,833,238 A | 9/1974 | Liard et al. | 3,972,320 A | 8/1976 | Kalman |
| 3,834,167 A | 9/1974 | Tabor | 3,973,753 A | 8/1976 | Wheeler |
| 3,834,739 A | 9/1974 | Abildgaard et al. | 3,973,858 A | 8/1976 | Poisson et al. |
| 3,835,523 A | 9/1974 | Stansfield et al. | 3,974,655 A | 8/1976 | Halpern et al. |
| 3,839,708 A | 10/1974 | Bredesen et al. | 3,974,865 A | 8/1976 | Fenton et al. |
| 3,842,483 A | 10/1974 | Cramer | 3,977,391 A | 8/1976 | Fleischmann |
| 3,842,668 A | 10/1974 | Lippke et al. | 3,980,871 A | 9/1976 | Lindstrom et al. |
| 3,845,664 A | 11/1974 | Perry, Jr. | 3,982,571 A | 9/1976 | Fenton et al. |
| 3,845,751 A | 11/1974 | Runstetler | 3,983,948 A | 10/1976 | Jeter |
| 3,845,757 A | 11/1974 | Weyer | 3,985,133 A | 10/1976 | Jenkins et al. |
| 3,847,434 A | 11/1974 | Weman et al. | 3,987,860 A | 10/1976 | Jabsen |
| 3,850,208 A | 11/1974 | Hamilton | 3,989,005 A | 11/1976 | Bowler, Jr. et al. |
| 3,853,117 A | 12/1974 | Murr | 3,991,749 A | 11/1976 | Zent |
| 3,854,469 A | 12/1974 | Giori et al. | 3,992,948 A | 11/1976 | D'Antonio et al. |
| 3,855,902 A | 12/1974 | Kirst et al. | 3,993,149 A | 11/1976 | Harvey |
| 3,857,399 A | 12/1974 | Zacouto et al. | 3,996,927 A | 12/1976 | Frank |
| 3,857,452 A | 12/1974 | Hartman | 3,996,962 A | 12/1976 | Sutherland |
| 3,857,745 A | 12/1974 | Grausch et al. | 4,003,141 A | 1/1977 | Le Roy |
| 3,858,581 A | 1/1975 | Kamen | 4,005,282 A | 1/1977 | Jennings |
| 3,863,622 A | 2/1975 | Buuck | 4,005,593 A | 2/1977 | Goldberg |
| 3,863,933 A | 2/1975 | Tredway | 4,006,735 A | 2/1977 | Hittman et al. |
| 3,867,950 A | 2/1975 | Fischell | 4,009,375 A | 2/1977 | White et al. |
| 3,868,008 A | 2/1975 | Brumbaugh | 4,009,591 A | 3/1977 | Hester |
| 3,868,679 A | 2/1975 | Arneson | 4,010,449 A | 3/1977 | Faggin et al. |
| 3,871,599 A | 3/1975 | Takada et al. | 4,014,319 A | 3/1977 | Favre et al. |
| 3,872,285 A | 3/1975 | Shum et al. | 4,014,321 A | 3/1977 | March |
| 3,874,388 A | 4/1975 | King et al. | 4,016,764 A | 4/1977 | Rice |
| 3,876,980 A | 4/1975 | Haemmig et al. | 4,017,329 A | 4/1977 | Larson |
| 3,878,908 A | 4/1975 | Andersson et al. | 4,018,134 A | 4/1977 | Linsinger et al. |
| 3,881,528 A | 5/1975 | Mackenzie | 4,022,190 A | 5/1977 | Meyer |
| 3,893,111 A | 7/1975 | Cotter | 4,024,864 A | 5/1977 | Davies et al. |
| 3,893,451 A | 7/1975 | Durand et al. | 4,025,912 A | 5/1977 | Rice |
| 3,895,681 A | 7/1975 | Griffin et al. | 4,026,276 A | 5/1977 | Chubbuck |
| 3,899,862 A | 8/1975 | Muys et al. | 4,027,661 A | 6/1977 | Lyon et al. |
| 3,904,234 A | 9/1975 | Hill et al. | 4,031,899 A | 6/1977 | Renirie et al. |
| 3,908,334 A | 9/1975 | Rychiger et al. | 4,036,775 A | 7/1977 | Trautvetter et al. |

| | | | | | | |
|---|---|---|---|---|---|---|
| 4,039,069 | A | 8/1977 | Kwan et al. | 4,168,567 A | 9/1979 | Leguy et al. |
| 4,041,954 | A | 8/1977 | Ohara et al. | 4,170,280 A | 10/1979 | Schwarz |
| 4,042,504 | A | 8/1977 | Drori et al. | 4,171,218 A | 10/1979 | Hoshino et al. |
| 4,045,345 | A | 8/1977 | Drori et al. | 4,183,124 A | 1/1980 | Hoffman |
| 4,047,851 | A | 9/1977 | Bender | 4,183,247 A | 1/1980 | Allen et al. |
| 4,048,494 | A | 9/1977 | Liesting et al. | 4,185,641 A | 1/1980 | Minior et al. |
| 4,048,879 | A | 9/1977 | Cox | 4,186,287 A | 1/1980 | Scott |
| 4,049,004 | A | 9/1977 | Walters | 4,186,749 A | 2/1980 | Fryer |
| 4,051,338 | A | 9/1977 | Harris, III | 4,186,751 A | 2/1980 | Fleischmann |
| 4,052,991 | A | 10/1977 | Zacouto et al. | 4,190,057 A | 2/1980 | Hill et al. |
| 4,055,074 | A | 10/1977 | Thimons et al. | 4,191,004 A | 3/1980 | Gmuer et al. |
| 4,055,175 | A | 10/1977 | Clemens et al. | 4,191,187 A | 3/1980 | Wright et al. |
| 4,056,854 | A | 11/1977 | Boretos et al. | 4,192,192 A | 3/1980 | Schnell |
| 4,058,007 | A | 11/1977 | Exner | 4,193,397 A | 3/1980 | Tucker et al. |
| 4,062,351 | A | 12/1977 | Hastwell et al. | 4,204,547 A | 5/1980 | Allocca |
| 4,062,354 | A | 12/1977 | Taylor et al. | 4,206,755 A | 6/1980 | Klein et al. |
| 4,062,360 | A | 12/1977 | Bentley | 4,206,761 A | 6/1980 | Cosman |
| 4,063,439 | A | 12/1977 | Besson et al. | 4,206,762 A | 6/1980 | Cosman |
| 4,064,882 | A | 12/1977 | Johnson et al. | 4,207,903 A | 6/1980 | O'Neill |
| 4,070,239 | A | 1/1978 | Bevilacqua | 4,212,074 A | 7/1980 | Kuno et al. |
| 4,072,047 | A | 2/1978 | Reismuller et al. | 4,217,221 A | 8/1980 | Masso |
| 4,073,292 | A | 2/1978 | Edelman | 4,217,588 A | 8/1980 | Freeny, Jr. |
| 4,075,099 | A | 2/1978 | Pelton et al. | 4,220,189 A | 9/1980 | Marquez |
| 4,075,602 | A | 2/1978 | Clothier | 4,221,219 A | 9/1980 | Tucker |
| 4,077,072 | A | 3/1978 | Dezura et al. | 4,221,523 A | 9/1980 | Eberle |
| 4,077,394 | A | 3/1978 | McCurdy | 4,223,837 A | 9/1980 | Gubbiotti et al. |
| 4,077,405 | A | 3/1978 | Haerten et al. | 4,226,124 A | 10/1980 | Kersten et al. |
| 4,077,882 | A | 3/1978 | Gangemi | 4,226,229 A | 10/1980 | Eckhart et al. |
| 4,078,620 | A | 3/1978 | Westlake et al. | 4,227,533 A | 10/1980 | Godfrey |
| 4,080,653 | A | 3/1978 | Barnes, Jr. et al. | 4,231,376 A | 11/1980 | Lyon et al. |
| 4,084,752 | A | 4/1978 | Hagiwara et al. | 4,232,682 A | 11/1980 | Veth |
| 4,086,488 | A | 4/1978 | Hill | 4,237,900 A | 12/1980 | Schulman et al. |
| 4,087,568 | A | 5/1978 | Fay et al. | 4,241,247 A | 12/1980 | Byrne et al. |
| 4,088,417 | A | 5/1978 | Kosmowski | 4,241,870 A | 12/1980 | Marcus |
| 4,089,329 | A | 5/1978 | Couvillon, Jr. et al. | 4,245,593 A | 1/1981 | Stein |
| 4,090,802 | A | 5/1978 | Bilz et al. | 4,246,877 A | 1/1981 | Kennedy |
| 4,092,719 | A | 5/1978 | Salmon et al. | 4,247,850 A | 1/1981 | Marcus |
| 4,092,925 | A | 6/1978 | Fromson | 4,248,238 A | 2/1981 | Joseph et al. |
| 4,096,866 | A | 6/1978 | Fischell | 4,248,241 A | 2/1981 | Tacchi |
| 4,098,293 | A | 7/1978 | Kramer et al. | 4,256,094 A | 3/1981 | Kapp et al. |
| 4,103,496 | A | 8/1978 | Colamussi et al. | 4,256,118 A | 3/1981 | Nagel et al. |
| 4,106,370 | A | 8/1978 | Kraus et al. | 4,262,343 A | 4/1981 | Claycomb |
| 4,107,689 | A | 8/1978 | Jellinek | 4,262,632 A | 4/1981 | Hanton et al. |
| 4,107,995 | A | 8/1978 | Ligman et al. | 4,265,241 A | 5/1981 | Portner et al. |
| 4,108,148 | A | 8/1978 | Cannon, III | 4,265,252 A | 5/1981 | Chubbuck et al. |
| 4,108,575 | A | 8/1978 | Schal et al. | 4,271,018 A | 6/1981 | Drori et al. |
| 4,109,148 | A | 8/1978 | Jaulmes et al. | 4,273,070 A | 6/1981 | Hoefelmayr et al. |
| 4,109,518 | A | 8/1978 | Dooley et al. | 4,274,444 A | 6/1981 | Ruyak |
| 4,109,644 | A | 8/1978 | Kojima | 4,275,600 A | 6/1981 | Turner et al. |
| 4,111,056 | A | 9/1978 | Mastromatteo | 4,275,913 A | 6/1981 | Marcus |
| 4,111,629 | A | 9/1978 | Nussbaumer et al. | 4,278,540 A | 7/1981 | Drori et al. |
| 4,114,424 | A | 9/1978 | Johnson | 4,280,036 A | 7/1981 | Fukatsu et al. |
| 4,114,606 | A | 9/1978 | Seylar | 4,280,775 A | 7/1981 | Wood |
| 4,120,097 | A | 10/1978 | Jeter | 4,281,666 A | 8/1981 | Cosman |
| 4,120,134 | A | 10/1978 | Scholle | 4,281,667 A | 8/1981 | Cosman |
| 4,121,635 | A | 10/1978 | Hansel | 4,284,073 A | 8/1981 | Krause et al. |
| 4,123,310 | A | 10/1978 | Varon et al. | 4,285,770 A | 8/1981 | Chi et al. |
| 4,124,023 | A | 11/1978 | Fleischmann et al. | 4,291,699 A | 9/1981 | Geddes et al. |
| 4,127,110 | A | 11/1978 | Bullara | 4,295,963 A | 10/1981 | Drori et al. |
| 4,130,169 | A | 12/1978 | Denison | 4,297,927 A | 11/1981 | Kuroda et al. |
| 4,131,596 | A | 12/1978 | Allen | 4,303,075 A | 12/1981 | Heilman et al. |
| 4,133,355 | A | 1/1979 | Mayer | 4,305,402 A | 12/1981 | Katims |
| 4,133,367 | A | 1/1979 | Abell | 4,312,374 A | 1/1982 | Drori et al. |
| 4,140,131 | A | 2/1979 | Dutcher et al. | 4,314,480 A | 2/1982 | Becker |
| 4,141,348 | A | 2/1979 | Hittman | 4,316,693 A | 2/1982 | Baxter et al. |
| 4,141,349 | A | 2/1979 | Ory et al. | 4,325,387 A | 4/1982 | Helfer |
| 4,143,661 | A | 3/1979 | LaForge et al. | 4,327,804 A | 5/1982 | Reed |
| 4,146,029 | A | 3/1979 | Ellinwood, Jr. | 4,328,654 A | 5/1982 | Van Ginkel et al. |
| 4,147,161 | A | 4/1979 | Ikebe et al. | 4,332,254 A | 6/1982 | Lundquist |
| 4,148,096 | A | 4/1979 | Haas et al. | 4,339,831 A | 7/1982 | Johnson |
| 4,149,423 | A | 4/1979 | Frosch et al. | 4,342,218 A | 8/1982 | Fox |
| 4,151,823 | A | 5/1979 | Grosse et al. | 4,342,308 A | 8/1982 | Trick |
| 4,153,085 | A | 5/1979 | Adams | 4,346,604 A | 8/1982 | Snook et al. |
| 4,156,422 | A | 5/1979 | Hildebrandt et al. | 4,347,851 A | 9/1982 | Jundanian |
| 4,160,448 | A | 7/1979 | Jackson | 4,350,647 A | 9/1982 | de la Cruz |
| 4,160,971 | A | 7/1979 | Jones et al. | 4,350,970 A | 9/1982 | von Tomkewitsch et al. |
| 4,166,469 | A | 9/1979 | Littleford | 4,351,037 A | 9/1982 | Scherbatskoy |
| 4,167,304 | A | 9/1979 | Gelbke | 4,351,116 A | 9/1982 | Scott, Jr. |
| 4,167,952 | A | 9/1979 | Reinicke | 4,356,486 A | 10/1982 | Mount |

| | | |
|---|---|---|
| 4,360,010 A | 11/1982 | Finney |
| 4,360,277 A | 11/1982 | Daniel et al. |
| 4,361,153 A | 11/1982 | Slocum et al. |
| 4,363,236 A | 12/1982 | Meyers |
| 4,364,276 A | 12/1982 | Shimazoe et al. |
| 4,365,425 A | 12/1982 | Gotchel |
| 4,368,937 A | 1/1983 | Palombo et al. |
| 4,369,013 A | 1/1983 | Abildgaard et al. |
| 4,373,527 A | 2/1983 | Fischell |
| 4,376,523 A | 3/1983 | Goyen et al. |
| 4,378,809 A | 4/1983 | Cosman |
| 4,380,427 A | 4/1983 | Hehl et al. |
| 4,385,636 A | 5/1983 | Cosman |
| 4,386,422 A | 5/1983 | Mumby et al. |
| 4,387,907 A | 6/1983 | Hiestand et al. |
| 4,392,368 A | 7/1983 | Folkesson et al. |
| 4,393,899 A | 7/1983 | Tsuji et al. |
| 4,393,951 A | 7/1983 | Horst-Rudolf et al. |
| 4,395,232 A | 7/1983 | Koch |
| 4,395,258 A | 7/1983 | Wang et al. |
| 4,395,916 A | 8/1983 | Martin |
| 4,398,983 A | 8/1983 | Suzuki et al. |
| 4,399,705 A | 8/1983 | Weiger et al. |
| 4,399,707 A | 8/1983 | Wamstad |
| 4,399,809 A | 8/1983 | Baro et al. |
| 4,399,821 A | 8/1983 | Bowers |
| 4,403,984 A | 9/1983 | Ash et al. |
| 4,404,968 A | 9/1983 | Evans, Sr. |
| 4,404,974 A | 9/1983 | Titus |
| 4,405,318 A | 9/1983 | Whitney et al. |
| 4,407,125 A | 10/1983 | Parsons |
| 4,407,271 A | 10/1983 | Schiff |
| 4,407,296 A | 10/1983 | Anderson |
| 4,407,326 A | 10/1983 | Wilhelm |
| 4,408,597 A | 10/1983 | Tenney, Jr. |
| 4,408,615 A | 10/1983 | Grossman |
| 4,415,071 A | 11/1983 | Butler et al. |
| 4,416,282 A | 11/1983 | Saulson et al. |
| 4,418,899 A | 12/1983 | Zimmermann et al. |
| 4,419,393 A | 12/1983 | Hanson et al. |
| 4,421,505 A | 12/1983 | Schwartz |
| 4,424,720 A | 1/1984 | Bucchianeri |
| 4,428,228 A | 1/1984 | Banzhaf et al. |
| 4,428,365 A | 1/1984 | Hakky et al. |
| 4,430,899 A | 2/1984 | Wessel et al. |
| 4,431,009 A | 2/1984 | Marino, Jr. et al. |
| 4,431,365 A | 2/1984 | Sturtz, Jr. |
| 4,432,363 A | 2/1984 | Kakegawa |
| 4,435,173 A | 3/1984 | Siposs et al. |
| 4,439,186 A | 3/1984 | Kuhl et al. |
| 4,441,491 A | 4/1984 | Evans, Sr. |
| 4,441,501 A | 4/1984 | Parent |
| 4,444,194 A | 4/1984 | Burcham |
| 4,444,498 A | 4/1984 | Heinemann |
| 4,445,385 A | 5/1984 | Endo |
| 4,446,711 A | 5/1984 | Valente |
| 4,447,224 A | 5/1984 | DeCant, Jr. et al. |
| 4,449,493 A | 5/1984 | Kopec et al. |
| 4,450,811 A | 5/1984 | Ichikawa et al. |
| 4,451,033 A | 5/1984 | Nestegard |
| 4,453,537 A | 6/1984 | Spitzer |
| 4,453,578 A | 6/1984 | Wilder |
| 4,460,835 A | 7/1984 | Masuoka et al. |
| 4,464,170 A | 8/1984 | Clemens et al. |
| 4,465,015 A | 8/1984 | Osta et al. |
| 4,465,474 A | 8/1984 | Mardorf et al. |
| 4,466,290 A | 8/1984 | Frick |
| 4,468,172 A | 8/1984 | Dixon et al. |
| 4,468,762 A | 8/1984 | Jurgens et al. |
| 4,469,365 A | 9/1984 | Marcus et al. |
| 4,471,182 A | 9/1984 | Wielgos et al. |
| 4,471,786 A | 9/1984 | Inagaki et al. |
| 4,473,067 A | 9/1984 | Schiff |
| 4,473,078 A | 9/1984 | Angel |
| 4,476,721 A | 10/1984 | Hochreuther et al. |
| 4,478,213 A | 10/1984 | Redding |
| 4,478,538 A | 10/1984 | Kakino et al. |
| 4,483,196 A | 11/1984 | Kurtz et al. |
| 4,484,135 A | 11/1984 | Ishihara et al. |
| 4,485,813 A | 12/1984 | Anderson et al. |
| 4,489,916 A | 12/1984 | Stevens |
| 4,492,632 A | 1/1985 | Mattson |
| 4,494,411 A | 1/1985 | Koschke et al. |
| 4,494,950 A | 1/1985 | Fischell |
| 4,497,176 A | 2/1985 | Rubin et al. |
| 4,497,201 A | 2/1985 | Allen et al. |
| 4,499,394 A | 2/1985 | Koal |
| 4,499,691 A | 2/1985 | Karazim et al. |
| 4,499,750 A | 2/1985 | Gerber et al. |
| 4,503,678 A | 3/1985 | Wimbush et al. |
| 4,511,974 A | 4/1985 | Nakane et al. |
| 4,513,295 A | 4/1985 | Jones et al. |
| 4,515,004 A | 5/1985 | Jaenson |
| 4,515,750 A | 5/1985 | Pardini et al. |
| 4,516,866 A | 5/1985 | Yamauchi et al. |
| 4,518,637 A | 5/1985 | Takeda et al. |
| 4,519,401 A | 5/1985 | Ko et al. |
| 4,520,443 A | 5/1985 | Yuki et al. |
| 4,522,213 A | 6/1985 | Wallroth et al. |
| 4,527,568 A | 7/1985 | Rickards et al. |
| 4,529,401 A | 7/1985 | Leslie et al. |
| 4,531,526 A | 7/1985 | Genest |
| 4,531,936 A | 7/1985 | Gordon |
| 4,536,000 A | 8/1985 | Rohm |
| 4,537,005 A | 8/1985 | Hoyland et al. |
| 4,537,129 A | 8/1985 | Heinemann et al. |
| 4,538,616 A | 9/1985 | Rogoff |
| 4,540,404 A | 9/1985 | Wolvek |
| 4,542,461 A | 9/1985 | Eldridge et al. |
| 4,544,369 A | 10/1985 | Skakoon et al. |
| 4,545,185 A | 10/1985 | Chikatani et al. |
| 4,546,524 A | 10/1985 | Kreft |
| 4,548,209 A | 10/1985 | Wielders et al. |
| 4,552,150 A | 11/1985 | Zacouto et al. |
| 4,553,226 A | 11/1985 | Scherbatskoy |
| 4,556,063 A | 12/1985 | Thompson et al. |
| 4,557,269 A | 12/1985 | Reynolds et al. |
| 4,557,332 A | 12/1985 | Denison et al. |
| 4,559,815 A | 12/1985 | Needham et al. |
| 4,560,979 A | 12/1985 | Rosskopf et al. |
| 4,561,442 A | 12/1985 | Vollmann et al. |
| 4,562,751 A | 1/1986 | Nason et al. |
| 4,563,175 A | 1/1986 | LaFond |
| 4,565,116 A | 1/1986 | Hehl et al. |
| 4,566,456 A | 1/1986 | Koning et al. |
| 4,569,623 A | 2/1986 | Goldmann |
| 4,570,351 A | 2/1986 | Szanto et al. |
| 4,571,161 A | 2/1986 | Leblanc et al. |
| 4,571,995 A | 2/1986 | Timme |
| 4,573,835 A | 3/1986 | Eckardt et al. |
| 4,574,792 A | 3/1986 | Trick |
| 4,576,181 A | 3/1986 | Wallace et al. |
| 4,576,183 A | 3/1986 | Plicchi et al. |
| 4,577,512 A | 3/1986 | Lowenheck et al. |
| 4,581,018 A | 4/1986 | Jassawalla et al. |
| 4,581,915 A | 4/1986 | Haulsee et al. |
| 4,587,840 A | 5/1986 | Dobler et al. |
| 4,589,805 A | 5/1986 | Duffner et al. |
| 4,592,339 A | 6/1986 | Kuzmak et al. |
| 4,592,340 A | 6/1986 | Boyles |
| 4,593,703 A | 6/1986 | Cosman |
| 4,595,228 A | 6/1986 | Chu |
| 4,596,563 A | 6/1986 | Pande |
| 4,599,943 A | 7/1986 | Kobler et al. |
| 4,600,855 A | 7/1986 | Strachan et al. |
| 4,602,541 A | 7/1986 | Benzinger et al. |
| 4,604,089 A | 8/1986 | Santangelo et al. |
| 4,605,354 A | 8/1986 | Daly |
| 4,606,419 A | 8/1986 | Perini |
| 4,606,478 A | 8/1986 | Hack et al. |
| 4,610,256 A | 9/1986 | Wallace |
| 4,614,137 A | 9/1986 | Jones |
| 4,617,016 A | 10/1986 | Blomberg et al. |
| 4,618,861 A | 10/1986 | Gettens et al. |
| 4,620,807 A | 11/1986 | Polit |
| 4,621,331 A | 11/1986 | Iwata et al. |
| 4,622,871 A | 11/1986 | Van Sickle et al. |
| 4,626,462 A | 12/1986 | Kober et al. |

| | | |
|---|---|---|
| 4,633,304 A | 12/1986 | Nagasaki et al. |
| 4,633,878 A | 1/1987 | Bombardieri et al. |
| 4,635,182 A | 1/1987 | Hintz |
| 4,637,736 A | 1/1987 | Andeen et al. |
| 4,638,665 A | 1/1987 | Benson et al. |
| 4,644,246 A | 2/1987 | Knapen et al. |
| 4,646,553 A | 3/1987 | Tufte et al. |
| 4,648,363 A | 3/1987 | Kronich |
| 4,648,406 A | 3/1987 | Miller |
| 4,658,358 A | 4/1987 | Leach et al. |
| 4,658,760 A | 4/1987 | Zebuhr |
| 4,660,568 A | 4/1987 | Cosman |
| 4,665,511 A | 5/1987 | Rodney et al. |
| 4,665,896 A | 5/1987 | LaForge et al. |
| 4,669,484 A | 6/1987 | Masters |
| 4,672,974 A | 6/1987 | Lee |
| 4,674,457 A | 6/1987 | Berger et al. |
| 4,674,546 A | 6/1987 | Fournier et al. |
| 4,678,408 A | 7/1987 | Nason et al. |
| 4,681,559 A | 7/1987 | Hooven |
| 4,683,850 A | 8/1987 | Bauder et al. |
| 4,685,463 A | 8/1987 | Williams |
| 4,685,469 A | 8/1987 | Keller et al. |
| 4,685,903 A | 8/1987 | Cable et al. |
| 4,686,987 A | 8/1987 | Salo et al. |
| 4,687,530 A | 8/1987 | Berscheid et al. |
| 4,689,979 A | 9/1987 | Otsuka et al. |
| 4,691,694 A | 9/1987 | Boyd et al. |
| 4,691,710 A | 9/1987 | Dickens et al. |
| 4,693,253 A | 9/1987 | Adams |
| 4,695,237 A | 9/1987 | Inaba et al. |
| 4,696,189 A | 9/1987 | Hochreuther et al. |
| 4,697,574 A | 10/1987 | Karcher et al. |
| 4,698,038 A | 10/1987 | Key et al. |
| 4,700,497 A | 10/1987 | Sato et al. |
| 4,700,610 A | 10/1987 | Bauer et al. |
| 4,701,143 A | 10/1987 | Key et al. |
| 4,703,756 A | 11/1987 | Gough et al. |
| 4,705,507 A | 11/1987 | Boyles |
| 4,706,948 A | 11/1987 | Kroecher et al. |
| 4,712,562 A | 12/1987 | Ohayon et al. |
| 4,718,425 A | 1/1988 | Tanaka et al. |
| 4,722,348 A | 2/1988 | Ligtenberg et al. |
| 4,724,806 A | 2/1988 | Hartwig et al. |
| 4,724,830 A | 2/1988 | Fischell |
| 4,725,826 A | 2/1988 | Hunter |
| 4,728,479 A | 3/1988 | Merkovsky |
| 4,729,517 A | 3/1988 | Krokor et al. |
| 4,730,188 A | 3/1988 | Milheiser |
| 4,730,420 A | 3/1988 | Stratmann et al. |
| 4,730,619 A | 3/1988 | Koning et al. |
| 4,731,058 A | 3/1988 | Doan |
| 4,735,205 A | 4/1988 | Chachques et al. |
| 4,738,267 A | 4/1988 | Lazorthes et al. |
| 4,738,268 A | 4/1988 | Kipnis |
| 4,741,345 A | 5/1988 | Matthews et al. |
| 4,741,732 A | 5/1988 | Crankshaw et al. |
| 4,743,129 A | 5/1988 | Keryhuel et al. |
| 4,745,541 A | 5/1988 | Vaniglia et al. |
| 4,746,830 A | 5/1988 | Holland |
| 4,750,495 A | 6/1988 | Moore et al. |
| 4,752,115 A | 6/1988 | Murray, Jr. et al. |
| 4,752,658 A | 6/1988 | Mack |
| 4,757,463 A | 7/1988 | Ballou et al. |
| 4,759,386 A | 7/1988 | Grouw, III |
| 4,763,649 A | 8/1988 | Merrick |
| 4,765,001 A | 8/1988 | Smith |
| 4,767,406 A | 8/1988 | Wadham et al. |
| 4,769,001 A | 9/1988 | Prince |
| 4,772,896 A | 9/1988 | Nakatsu et al. |
| 4,773,401 A | 9/1988 | Citak et al. |
| 4,774,950 A | 10/1988 | Cohen |
| 4,774,955 A | 10/1988 | Jones |
| 4,777,953 A | 10/1988 | Ash et al. |
| 4,779,626 A | 10/1988 | Peel et al. |
| 4,781,192 A | 11/1988 | Demer |
| 4,782,826 A | 11/1988 | Fogarty |
| 4,783,106 A | 11/1988 | Nutter |
| 4,788,847 A | 12/1988 | Sterghos |
| 4,791,318 A | 12/1988 | Lewis et al. |
| 4,794,803 A | 1/1989 | Osterhout et al. |
| 4,796,641 A | 1/1989 | Mills et al. |
| 4,798,211 A | 1/1989 | Goor et al. |
| 4,798,227 A | 1/1989 | Goodwin |
| 4,799,491 A | 1/1989 | Eckerle |
| 4,799,625 A | 1/1989 | Weaver, Jr. et al. |
| 4,802,488 A | 2/1989 | Eckerle |
| 4,803,987 A | 2/1989 | Calfee et al. |
| 4,804,368 A | 2/1989 | Skakoon et al. |
| 4,807,321 A | 2/1989 | Grasselli et al. |
| 4,808,167 A | 2/1989 | Mann et al. |
| 4,812,823 A | 3/1989 | Dickerson |
| 4,819,656 A | 4/1989 | Spector |
| 4,820,265 A | 4/1989 | DeSatnick et al. |
| 4,820,953 A | 4/1989 | Saubolle et al. |
| 4,821,167 A | 4/1989 | Wiebe |
| 4,821,723 A | 4/1989 | Baker, Jr. et al. |
| 4,823,779 A | 4/1989 | Daly et al. |
| 4,830,006 A | 5/1989 | Haluska et al. |
| 4,832,034 A | 5/1989 | Pizziconi et al. |
| 4,833,384 A | 5/1989 | Munro et al. |
| 4,834,731 A | 5/1989 | Nowak et al. |
| 4,838,857 A | 6/1989 | Strowe et al. |
| 4,840,068 A | 6/1989 | Mayhew, Jr. |
| 4,840,350 A | 6/1989 | Cook et al. |
| 4,844,002 A | 7/1989 | Yasui et al. |
| 4,846,153 A | 7/1989 | Berci |
| 4,846,191 A | 7/1989 | Brockway et al. |
| 4,846,664 A | 7/1989 | Hehl et al. |
| 4,854,328 A | 8/1989 | Pollack |
| 4,863,470 A | 9/1989 | Carter |
| 4,865,587 A | 9/1989 | Walling |
| 4,867,160 A | 9/1989 | Schaldach et al. |
| 4,867,498 A | 9/1989 | Delphia et al. |
| 4,867,618 A | 9/1989 | Brohammer |
| 4,869,252 A | 9/1989 | Gilli |
| 4,870,258 A | 9/1989 | Mochizuki et al. |
| 4,871,351 A | 10/1989 | Feingold |
| 4,872,483 A | 10/1989 | Shah |
| 4,872,869 A | 10/1989 | Johns |
| 4,873,677 A | 10/1989 | Sakamoto et al. |
| 4,875,483 A | 10/1989 | Vollmann et al. |
| 4,880,004 A | 11/1989 | Baker, Jr. et al. |
| 4,882,678 A | 11/1989 | Hollis et al. |
| 4,886,392 A | 12/1989 | Iio et al. |
| 4,895,151 A | 1/1990 | Grevis et al. |
| 4,896,594 A | 1/1990 | Baur et al. |
| 4,898,158 A | 2/1990 | Daly et al. |
| 4,898,578 A | 2/1990 | Rubalcaba, Jr. |
| 4,899,751 A | 2/1990 | Cohen |
| 4,899,752 A | 2/1990 | Cohen |
| 4,902,277 A | 2/1990 | Mathies et al. |
| 4,903,701 A | 2/1990 | Moore et al. |
| 4,909,678 A | 3/1990 | Kakimoto et al. |
| 4,913,147 A | 4/1990 | Fahlstrom et al. |
| 4,919,143 A | 4/1990 | Ayers |
| 4,924,872 A | 5/1990 | Frank |
| 4,926,903 A | 5/1990 | Kawai et al. |
| 4,932,406 A | 6/1990 | Berkovits |
| 4,934,369 A | 6/1990 | Maxwell |
| 4,936,304 A | 6/1990 | Kresh et al. |
| 4,940,037 A | 7/1990 | Eckert et al. |
| 4,941,718 A | 7/1990 | Alexander, III et al. |
| 4,942,004 A | 7/1990 | Catanzaro |
| 4,944,050 A | 7/1990 | Shames et al. |
| 4,944,298 A | 7/1990 | Sholder |
| 4,944,307 A | 7/1990 | Hon et al. |
| 4,945,761 A | 8/1990 | Lessi et al. |
| 4,949,724 A | 8/1990 | Mahutte et al. |
| 4,952,205 A | 8/1990 | Mauerer et al. |
| 4,952,928 A | 8/1990 | Carroll et al. |
| 4,953,563 A | 9/1990 | Kaiser et al. |
| 4,954,677 A | 9/1990 | Alberter et al. |
| 4,958,630 A | 9/1990 | Rosenbluth et al. |
| 4,958,645 A | 9/1990 | Cadell et al. |
| 4,960,424 A | 10/1990 | Grooters |
| 4,960,966 A | 10/1990 | Evans et al. |
| 4,967,585 A | 11/1990 | Grimaldo |

| Patent | Date | Name |
|---|---|---|
| 4,967,761 A | 11/1990 | Nathanielsz |
| 4,970,823 A | 11/1990 | Chen et al. |
| 4,971,251 A | 11/1990 | Dobrick et al. |
| 4,977,896 A | 12/1990 | Robinson et al. |
| 4,978,335 A | 12/1990 | Arthur, III |
| 4,978,338 A | 12/1990 | Melsky et al. |
| 4,979,730 A | 12/1990 | Holbrook et al. |
| 4,980,671 A | 12/1990 | McCurdy |
| 4,981,141 A | 1/1991 | Segalowitz |
| 4,981,173 A | 1/1991 | Perkins et al. |
| 4,981,426 A | 1/1991 | Aoki et al. |
| 4,987,897 A | 1/1991 | Funke et al. |
| 4,988,337 A | 1/1991 | Ito et al. |
| 4,992,794 A | 2/1991 | Brouwers et al. |
| 4,997,556 A | 3/1991 | Yano et al. |
| 5,001,528 A | 3/1991 | Bahraman |
| 5,003,807 A | 4/1991 | Terrell et al. |
| 5,003,975 A | 4/1991 | Hafelfinger et al. |
| 5,003,976 A | 4/1991 | Alt et al. |
| 5,004,472 A | 4/1991 | Wallace |
| 5,004,873 A | 4/1991 | Schnut |
| 5,005,574 A | 4/1991 | Fearnot et al. |
| 5,005,586 A | 4/1991 | Lahr |
| 5,006,844 A | 4/1991 | Ohta et al. |
| 5,007,401 A | 4/1991 | Grohn et al. |
| 5,007,430 A | 4/1991 | Dardik |
| 5,007,919 A | 4/1991 | Silva et al. |
| 5,009,662 A | 4/1991 | Wallace et al. |
| 5,010,893 A | 4/1991 | Sholder |
| 5,012,286 A | 4/1991 | Kawano et al. |
| 5,012,810 A | 5/1991 | Strand et al. |
| 5,013,292 A | 5/1991 | Lemay et al. |
| 5,014,040 A | 5/1991 | Weaver et al. |
| 5,019,032 A | 5/1991 | Robertson |
| 5,019,041 A | 5/1991 | Robinson et al. |
| 5,020,845 A | 6/1991 | Falcoff et al. |
| 5,021,046 A | 6/1991 | Wallace |
| 5,022,395 A | 6/1991 | Russie |
| 5,024,965 A | 6/1991 | Chang et al. |
| 5,026,180 A | 6/1991 | Tajima et al. |
| 5,026,360 A | 6/1991 | Johnsen et al. |
| 5,028,918 A | 7/1991 | Giles et al. |
| 5,032,822 A | 7/1991 | Sweet |
| 5,036,869 A | 8/1991 | Inahara et al. |
| 5,038,800 A | 8/1991 | Oba et al. |
| 5,041,086 A | 8/1991 | Koenig et al. |
| 5,041,826 A | 8/1991 | Milheiser |
| 5,042,503 A | 8/1991 | Torok et al. |
| 5,044,770 A | 9/1991 | Haghkar |
| 5,046,661 A | 9/1991 | Kimura et al. |
| 5,048,060 A | 9/1991 | Arai et al. |
| 5,050,922 A | 9/1991 | Falcoff |
| 5,052,910 A | 10/1991 | Hehl et al. |
| 5,053,008 A | 10/1991 | Bajaj |
| 5,057,078 A | 10/1991 | Foote et al. |
| 5,058,583 A | 10/1991 | Geddes et al. |
| 5,061,239 A | 10/1991 | Shiels |
| 5,062,052 A | 10/1991 | Sparer et al. |
| 5,062,053 A | 10/1991 | Shirai et al. |
| 5,062,559 A | 11/1991 | Falcoff |
| 5,064,974 A | 11/1991 | Vigneau et al. |
| 5,067,960 A | 11/1991 | Grandjean et al. |
| 5,068,779 A | 11/1991 | Sullivan et al. |
| 5,069,680 A | 12/1991 | Grandjean et al. |
| 5,077,102 A | 12/1991 | Chong |
| 5,077,870 A | 1/1992 | Melbye et al. |
| 5,078,139 A | 1/1992 | Strand et al. |
| 5,082,006 A | 1/1992 | Jonasson et al. |
| 5,083,563 A | 1/1992 | Collins et al. |
| 5,084,699 A | 1/1992 | DeMichele |
| 5,085,224 A | 2/1992 | Galen et al. |
| 5,085,258 A | 2/1992 | Fink, Jr. et al. |
| 5,089,673 A | 2/1992 | Strzodka et al. |
| 5,089,979 A | 2/1992 | McEachern et al. |
| 5,095,309 A | 3/1992 | Troyk et al. |
| 5,096,271 A | 3/1992 | Portman |
| 5,097,831 A | 3/1992 | Lekholm |
| 5,098,384 A | 3/1992 | Abrams |
| 5,103,832 A | 4/1992 | Jackson |
| 5,105,810 A | 4/1992 | Collins et al. |
| 5,107,850 A | 4/1992 | Olive |
| 5,112,344 A | 5/1992 | Petros et al. |
| 5,113,859 A | 5/1992 | Funke et al. |
| 5,113,869 A | 5/1992 | Nappholz et al. |
| 5,115,676 A | 5/1992 | Lee |
| 5,117,825 A | 6/1992 | Grevious |
| 5,121,777 A | 6/1992 | Leininger et al. |
| 5,127,451 A | 7/1992 | Fink, Jr. et al. |
| 5,129,394 A | 7/1992 | Mehra |
| 5,129,806 A | 7/1992 | Hehl et al. |
| 5,131,145 A | 7/1992 | Badoureaux et al. |
| 5,131,388 A | 7/1992 | Pless et al. |
| 5,133,358 A | 7/1992 | Gustafson et al. |
| 5,135,488 A | 8/1992 | Foote et al. |
| 5,139,484 A | 8/1992 | Hazon et al. |
| 5,144,949 A | 9/1992 | Olson |
| 5,148,580 A | 9/1992 | Dyckow et al. |
| 5,148,695 A | 9/1992 | Ellis |
| 5,152,770 A | 10/1992 | Bengmark et al. |
| 5,152,776 A | 10/1992 | Pinchuk |
| 5,154,170 A | 10/1992 | Bennett et al. |
| 5,154,171 A | 10/1992 | Chirife et al. |
| 5,154,693 A | 10/1992 | East et al. |
| 5,156,972 A | 10/1992 | Issachar |
| 5,158,078 A | 10/1992 | Bennett et al. |
| 5,163,429 A | 11/1992 | Cohen |
| 5,167,615 A | 12/1992 | East et al. |
| 5,168,757 A | 12/1992 | Rabenau et al. |
| 5,168,982 A | 12/1992 | Hakanen et al. |
| 5,171,299 A | 12/1992 | Heitzmann et al. |
| 5,173,873 A | 12/1992 | Wu et al. |
| 5,174,286 A | 12/1992 | Chirife et al. |
| 5,174,291 A | 12/1992 | Schoonen et al. |
| 5,176,502 A | 1/1993 | Sanderson et al. |
| 5,178,197 A | 1/1993 | Healy |
| 5,181,423 A | 1/1993 | Philipps et al. |
| 5,181,517 A | 1/1993 | Hickey |
| 5,184,132 A | 2/1993 | Baird |
| 5,184,614 A | 2/1993 | Collins et al. |
| 5,184,619 A | 2/1993 | Austin |
| 5,185,535 A | 2/1993 | Farb et al. |
| 5,186,224 A | 2/1993 | Schirmacher et al. |
| 5,188,106 A | 2/1993 | Nappholz et al. |
| 5,188,604 A | 2/1993 | Orth |
| 5,192,314 A | 3/1993 | Daskalakis |
| 5,195,362 A | 3/1993 | Eason |
| 5,197,322 A | 3/1993 | Indravudh |
| 5,199,427 A | 4/1993 | Strickland |
| 5,199,428 A | 4/1993 | Obel et al. |
| 5,201,753 A | 4/1993 | Lampropoulos et al. |
| 5,204,670 A | 4/1993 | Stinton |
| 5,207,429 A | 5/1993 | Walmsley et al. |
| 5,209,223 A | 5/1993 | McGorry et al. |
| 5,209,732 A | 5/1993 | Lampropoulos et al. |
| 5,211,129 A | 5/1993 | Taylor et al. |
| 5,211,161 A | 5/1993 | Stef et al. |
| 5,212,476 A | 5/1993 | Maloney |
| 5,213,331 A | 5/1993 | Avanzini |
| 5,215,523 A | 6/1993 | Williams et al. |
| 5,218,343 A | 6/1993 | Stobbe et al. |
| 5,218,957 A | 6/1993 | Strickland |
| 5,226,429 A | 7/1993 | Kuzmak |
| 5,226,604 A | 7/1993 | Seiffert et al. |
| 5,230,694 A | 7/1993 | Rosenblum |
| 5,233,985 A | 8/1993 | Hudrlik |
| 5,235,326 A | 8/1993 | Beigel et al. |
| 5,244,269 A | 9/1993 | Harriehausen et al. |
| 5,244,461 A | 9/1993 | Derlien et al. |
| 5,246,008 A | 9/1993 | Mueller et al. |
| 5,249,858 A | 10/1993 | Nusser |
| 5,250,020 A | 10/1993 | Bley |
| 5,254,096 A | 10/1993 | Rondelet et al. |
| 5,256,157 A | 10/1993 | Samiotes et al. |
| 5,263,244 A | 11/1993 | Centa et al. |
| 5,263,981 A | 11/1993 | Polyak et al. |
| 5,267,940 A | 12/1993 | Moulder |
| 5,267,942 A | 12/1993 | Saperston |
| 5,269,891 A | 12/1993 | Colin et al. |

| Patent | Date | Inventors |
|---|---|---|
| 5,271,395 A | 12/1993 | Wahlstrand et al. |
| 5,274,859 A | 1/1994 | Redman et al. |
| 5,280,789 A | 1/1994 | Potts |
| 5,282,839 A | 2/1994 | Roline et al. |
| 5,282,840 A | 2/1994 | Hudrlik |
| 5,291,894 A | 3/1994 | Nagy et al. |
| 5,292,219 A | 3/1994 | Merin et al. |
| 5,295,967 A | 3/1994 | Rondelet et al. |
| 5,298,022 A | 3/1994 | Bernardi et al. |
| 5,298,884 A | 3/1994 | Gilmore et al. |
| 5,300,093 A | 4/1994 | Koestner et al. |
| 5,300,120 A | 4/1994 | Knapp et al. |
| 5,304,112 A | 4/1994 | Mrklas et al. |
| 5,305,923 A | 4/1994 | Kirschner et al. |
| 5,312,443 A | 5/1994 | Adams et al. |
| 5,312,452 A | 5/1994 | Salo |
| 5,312,453 A | 5/1994 | Shelton et al. |
| 5,313,953 A | 5/1994 | Yomtov et al. |
| 5,314,451 A | 5/1994 | Mulier |
| 5,314,457 A | 5/1994 | Jeutter et al. |
| 5,324,315 A | 6/1994 | Grevious |
| 5,325,834 A | 7/1994 | Ballheimer et al. |
| 5,326,249 A | 7/1994 | Weissfloch et al. |
| 5,328,460 A | 7/1994 | Lord et al. |
| 5,330,511 A | 7/1994 | Boute et al. |
| 5,337,750 A | 8/1994 | Walloch |
| 5,341,430 A | 8/1994 | Aulia et al. |
| 5,342,401 A | 8/1994 | Spano et al. |
| 5,342,406 A | 8/1994 | Thompson |
| 5,344,388 A | 9/1994 | Maxwell et al. |
| 5,347,476 A | 9/1994 | McBean, Sr. |
| 5,348,210 A | 9/1994 | Linzell et al. |
| 5,348,536 A | 9/1994 | Young et al. |
| 5,350,413 A | 9/1994 | Miller et al. |
| 5,352,180 A | 10/1994 | Candelon et al. |
| 5,353,622 A | 10/1994 | Theener |
| 5,353,800 A | 10/1994 | Pohndorf et al. |
| 5,354,200 A | 10/1994 | Klein et al. |
| 5,354,316 A | 10/1994 | Keimel |
| 5,354,319 A | 10/1994 | Wyborny et al. |
| 5,360,407 A | 11/1994 | Leonard et al. |
| 5,365,462 A | 11/1994 | McBean, Sr. |
| 5,365,619 A | 11/1994 | Solomon |
| 5,365,985 A | 11/1994 | Todd et al. |
| 5,368,040 A | 11/1994 | Carney |
| 5,370,665 A | 12/1994 | Hudrlik |
| 5,373,852 A | 12/1994 | Harrison et al. |
| 5,375,073 A | 12/1994 | McBean |
| 5,377,128 A | 12/1994 | McBean |
| 5,378,231 A | 1/1995 | Johnson et al. |
| 5,382,232 A | 1/1995 | Hague et al. |
| 5,383,915 A | 1/1995 | Adams |
| 5,388,578 A | 2/1995 | Yomtov et al. |
| 5,388,586 A | 2/1995 | Lee et al. |
| 5,388,831 A | 2/1995 | Quadri et al. |
| 5,394,909 A | 3/1995 | Mitchell et al. |
| 5,402,944 A | 4/1995 | Pape et al. |
| 5,406,957 A | 4/1995 | Tansey |
| 5,409,009 A | 4/1995 | Olson |
| 5,411,031 A | 5/1995 | Yomtov |
| 5,411,551 A | 5/1995 | Winston et al. |
| 5,411,552 A | 5/1995 | Andersen et al. |
| 5,416,372 A | 5/1995 | Ljungstroem et al. |
| 5,417,226 A | 5/1995 | Juma |
| 5,417,717 A | 5/1995 | Salo et al. |
| 5,425,362 A | 6/1995 | Siker et al. |
| 5,431,171 A | 7/1995 | Harrison et al. |
| 5,431,694 A | 7/1995 | Snaper et al. |
| 5,433,694 A | 7/1995 | Lim et al. |
| 5,437,605 A | 8/1995 | Helmy et al. |
| 5,443,215 A | 8/1995 | Fackler |
| 5,447,519 A | 9/1995 | Peterson |
| 5,449,368 A | 9/1995 | Kuzmak |
| 5,456,690 A | 10/1995 | Duong-Van |
| 5,461,390 A | 10/1995 | Hoshen |
| 5,464,435 A | 11/1995 | Neumann |
| 5,467,627 A | 11/1995 | Smith et al. |
| 5,474,226 A | 12/1995 | Joseph |
| 5,479,818 A | 1/1996 | Walter et al. |
| 5,482,049 A | 1/1996 | Addiss et al. |
| 5,487,760 A | 1/1996 | Villafana |
| 5,493,738 A | 2/1996 | Sanderson et al. |
| 5,494,036 A | 2/1996 | Uber, III et al. |
| 5,494,193 A | 2/1996 | Kirschner et al. |
| 5,504,474 A | 4/1996 | Libman et al. |
| 5,505,916 A | 4/1996 | Berry, Jr. |
| 5,507,412 A | 4/1996 | Ebert et al. |
| 5,507,737 A | 4/1996 | Palmskog et al. |
| 5,507,785 A | 4/1996 | Deno |
| 5,509,888 A | 4/1996 | Miller |
| 5,509,891 A | 4/1996 | DeRidder |
| 5,513,945 A | 5/1996 | Hartmann et al. |
| 5,514,103 A | 5/1996 | Srisathapat et al. |
| 5,518,504 A | 5/1996 | Polyak |
| 5,520,606 A | 5/1996 | Schoolman et al. |
| 5,523,740 A | 6/1996 | Burgmann et al. |
| 5,534,018 A | 7/1996 | Wahlstrand et al. |
| 5,535,752 A | 7/1996 | Halperin et al. |
| 5,538,005 A | 7/1996 | Harrison et al. |
| 5,541,857 A | 7/1996 | Walter et al. |
| 5,545,140 A | 8/1996 | Conero et al. |
| 5,545,151 A | 8/1996 | O'Connor et al. |
| 5,545,186 A | 8/1996 | Olson et al. |
| 5,545,214 A | 8/1996 | Stevens |
| 5,547,470 A | 8/1996 | Johnson et al. |
| 5,551,427 A | 9/1996 | Altman |
| 5,551,439 A | 9/1996 | Hickey |
| 5,554,185 A | 9/1996 | Block et al. |
| 5,558,644 A | 9/1996 | Boyd et al. |
| 5,564,434 A | 10/1996 | Halperin et al. |
| 5,575,770 A | 11/1996 | Melsky et al. |
| 5,584,803 A | 12/1996 | Stevens et al. |
| 5,586,629 A | 12/1996 | Shoberg et al. |
| 5,593,430 A | 1/1997 | Renger |
| 5,594,665 A | 1/1997 | Walter et al. |
| 5,596,986 A | 1/1997 | Goldfarb |
| 5,597,284 A | 1/1997 | Weltlich et al. |
| 5,610,083 A | 3/1997 | Chan et al. |
| 5,611,768 A | 3/1997 | Tutrone, Jr. |
| 5,612,497 A | 3/1997 | Walter et al. |
| 5,615,671 A | 4/1997 | Schoonen et al. |
| 5,619,991 A | 4/1997 | Sloane |
| 5,625,946 A | 5/1997 | Wildeson et al. |
| 5,626,623 A | 5/1997 | Kieval et al. |
| 5,626,630 A | 5/1997 | Markowitz et al. |
| 5,630,836 A | 5/1997 | Prem et al. |
| 5,634,255 A | 6/1997 | Bishop et al. |
| 5,637,083 A | 6/1997 | Bertrand et al. |
| 5,643,207 A | 7/1997 | Rise |
| 5,645,116 A | 7/1997 | McDonald |
| 5,650,766 A | 7/1997 | Burgmann et al. |
| 5,673,585 A | 10/1997 | Bishop et al. |
| 5,676,690 A | 10/1997 | Noren et al. |
| 5,681,285 A | 10/1997 | Ford et al. |
| 5,686,831 A | 11/1997 | Vandervalk et al. |
| 5,687,734 A | 11/1997 | Dempsey et al. |
| 5,693,076 A | 12/1997 | Kaemmerer |
| 5,702,368 A | 12/1997 | Stevens et al. |
| 5,702,427 A | 12/1997 | Ecker et al. |
| 5,702,431 A | 12/1997 | Wang et al. |
| 5,704,352 A | 1/1998 | Tremblay et al. |
| 5,715,786 A | 2/1998 | Seiberth et al. |
| 5,715,837 A | 2/1998 | Chen |
| 5,720,436 A | 2/1998 | Buschor et al. |
| 5,730,101 A | 3/1998 | Aupperle et al. |
| 5,732,710 A | 3/1998 | Rabinovich et al. |
| 5,733,313 A | 3/1998 | Barreras, Sr. et al. |
| 5,738,652 A | 4/1998 | Boyd et al. |
| 5,742,233 A | 4/1998 | Hoffman et al. |
| 5,743,267 A | 4/1998 | Nikolic et al. |
| 5,749,369 A | 5/1998 | Rabinovich et al. |
| 5,749,909 A | 5/1998 | Schroeppel et al. |
| 5,755,687 A | 5/1998 | Donlon |
| 5,755,748 A | 5/1998 | Borza et al. |
| 5,765,568 A | 6/1998 | Sweezer, Jr. et al. |
| 5,769,812 A | 6/1998 | Stevens et al. |
| 5,771,903 A | 6/1998 | Jakobsson |
| 5,782,774 A | 7/1998 | Shmulewitz |

| | | |
|---|---|---|
| 5,787,520 A | 8/1998 | Dunbar |
| 5,791,344 A | 8/1998 | Schulman et al. |
| 5,792,094 A | 8/1998 | Stevens et al. |
| 5,792,179 A | 8/1998 | Sideris |
| 5,795,325 A | 8/1998 | Valley et al. |
| 5,796,827 A | 8/1998 | Coppersmith et al. |
| 5,800,375 A | 9/1998 | Sweezer et al. |
| 5,807,265 A | 9/1998 | Itoigawa et al. |
| 5,807,336 A | 9/1998 | Russo et al. |
| 5,810,015 A | 9/1998 | Flaherty |
| 5,810,757 A | 9/1998 | Sweezer, Jr. et al. |
| 5,814,016 A | 9/1998 | Valley et al. |
| 5,817,093 A | 10/1998 | Williamson, IV et al. |
| 5,833,603 A | 11/1998 | Kovacs et al. |
| 5,836,300 A | 11/1998 | Mault |
| 5,836,886 A | 11/1998 | Itoigawa et al. |
| 5,840,081 A | 11/1998 | Andersen et al. |
| 5,849,225 A | 12/1998 | Ebina et al. |
| 5,855,597 A | 1/1999 | Jayaraman et al. |
| 5,855,601 A | 1/1999 | Bessler et al. |
| 5,860,938 A | 1/1999 | Lafontaine et al. |
| 5,861,018 A | 1/1999 | Feierbach |
| 5,863,366 A | 1/1999 | Snow |
| 5,868,702 A | 2/1999 | Stevens et al. |
| 5,873,837 A | 2/1999 | Lieber et al. |
| 5,875,953 A | 3/1999 | Shioya et al. |
| 5,879,499 A | 3/1999 | Corvi |
| 5,881,919 A | 3/1999 | Womac et al. |
| 5,885,238 A | 3/1999 | Stevens et al. |
| 5,887,475 A | 3/1999 | Muldner |
| 5,899,927 A | 5/1999 | Ecker et al. |
| 5,916,179 A | 6/1999 | Sharrock |
| 5,916,237 A | 6/1999 | Schu |
| 5,935,078 A | 8/1999 | Feierbach |
| 5,938,669 A | 8/1999 | Klaiber et al. |
| 5,951,487 A | 9/1999 | Brehmeier-Flick et al. |
| 5,957,861 A | 9/1999 | Combs et al. |
| 5,967,986 A | 10/1999 | Cimochowski et al. |
| 5,971,934 A | 10/1999 | Scherer et al. |
| 5,974,873 A | 11/1999 | Nelson et al. |
| 5,978,985 A | 11/1999 | Thurman |
| 5,995,874 A | 11/1999 | Borza et al. |
| 6,015,386 A | 1/2000 | Kensey et al. |
| 6,015,387 A | 1/2000 | Schwartz et al. |
| 6,019,729 A | 2/2000 | Itoigawa et al. |
| 6,024,704 A | 2/2000 | Meador et al. |
| 6,030,413 A | 2/2000 | Lazarus |
| 6,035,461 A | 3/2000 | Nguyen |
| 6,053,873 A | 4/2000 | Govari et al. |
| 6,056,723 A | 5/2000 | Donlon |
| 6,058,330 A | 5/2000 | Borza et al. |
| 6,059,757 A | 5/2000 | Macoviak et al. |
| 6,067,474 A | 5/2000 | Schulman et al. |
| 6,067,991 A | 5/2000 | Forsell et al. |
| 6,076,016 A | 6/2000 | Feierbach |
| 6,083,174 A | 7/2000 | Brehmeier-Flick et al. |
| 6,090,096 A | 7/2000 | St. Goar et al. |
| 6,102,678 A | 8/2000 | Peclat et al. |
| 6,102,856 A | 8/2000 | Groff et al. |
| 6,102,922 A | 8/2000 | Jakobsson et al. |
| 6,106,477 A | 8/2000 | Miesel et al. |
| 6,106,551 A | 8/2000 | Crossett et al. |
| 6,110,145 A | 8/2000 | Macoviak |
| 6,113,553 A | 9/2000 | Chubbuck |
| 6,131,664 A | 10/2000 | Sonnier |
| 6,135,945 A | 10/2000 | Sultan |
| 6,159,156 A | 12/2000 | Van Bockel et al. |
| 6,162,180 A | 12/2000 | Miesel et al. |
| 6,162,245 A | 12/2000 | Jayaraman et al. |
| 6,168,614 B1 | 1/2001 | Andersen et al. |
| 6,234,745 B1 | 5/2001 | Pugh et al. |
| 6,240,316 B1 | 5/2001 | Richmond et al. |
| 6,240,318 B1 | 5/2001 | Phillips |
| 6,245,102 B1 | 6/2001 | Jayaraman |
| 6,248,080 B1 | 6/2001 | Miesel et al. |
| 6,251,093 B1 | 6/2001 | Valley et al. |
| 6,269,819 B1 | 8/2001 | Oz et al. |
| 6,277,078 B1 | 8/2001 | Porat et al. |
| 6,292,697 B1 | 9/2001 | Roberts |
| 6,309,350 B1 | 10/2001 | VanTassel et al. |
| 6,315,769 B1 | 11/2001 | Peer et al. |
| 6,319,208 B1 | 11/2001 | Abita et al. |
| 6,328,699 B1 | 12/2001 | Eigler et al. |
| 6,338,735 B1 | 1/2002 | Stevens |
| 6,357,438 B1 | 3/2002 | Hansen |
| 6,360,122 B1 | 3/2002 | Fischell et al. |
| 6,360,822 B1 | 3/2002 | Robertson et al. |
| 6,366,817 B1 | 4/2002 | Kung |
| 6,379,308 B1 | 4/2002 | Brockway et al. |
| 6,379,380 B1 | 4/2002 | Satz |
| 6,398,752 B1 | 6/2002 | Sweezer, Jr. et al. |
| 6,409,674 B1 | 6/2002 | Brockway et al. |
| 6,423,031 B1 | 7/2002 | Donlon |
| 6,430,444 B1 | 8/2002 | Borza et al. |
| 6,431,175 B1 | 8/2002 | Penner et al. |
| 6,432,040 B1 | 8/2002 | Meah |
| 6,443,887 B1 | 9/2002 | Derus et al. |
| 6,443,893 B1 | 9/2002 | Schnakenberg et al. |
| 6,450,173 B1 | 9/2002 | Forsell et al. |
| 6,450,946 B1 | 9/2002 | Forsell et al. |
| 6,453,907 B1 | 9/2002 | Forsell et al. |
| 6,454,698 B1 | 9/2002 | Forsell et al. |
| 6,454,699 B1 | 9/2002 | Forsell et al. |
| 6,454,700 B1 | 9/2002 | Forsell et al. |
| 6,454,701 B1 | 9/2002 | Forsell et al. |
| 6,461,292 B1 | 10/2002 | Forsell et al. |
| 6,461,293 B1 | 10/2002 | Forsell et al. |
| 6,463,329 B1 | 10/2002 | Goedeke |
| 6,463,935 B1 | 10/2002 | Forsell et al. |
| 6,464,628 B1 | 10/2002 | Forsell et al. |
| 6,470,212 B1 | 10/2002 | Weijand et al. |
| 6,470,892 B1 | 10/2002 | Forsell et al. |
| 6,471,635 B1 | 10/2002 | Forsell et al. |
| 6,475,136 B1 | 11/2002 | Forsell et al. |
| 6,475,170 B1 | 11/2002 | Doron et al. |
| 6,482,145 B1 | 11/2002 | Forsell et al. |
| 6,482,171 B1 | 11/2002 | Corvi et al. |
| 6,482,177 B1 | 11/2002 | Leinders et al. |
| 6,486,588 B2 | 11/2002 | Doron et al. |
| 6,503,189 B1 | 1/2003 | Forsell et al. |
| 6,504,286 B1 | 1/2003 | Porat et al. |
| 6,531,739 B2 | 3/2003 | Cable et al. |
| 6,533,719 B2 | 3/2003 | Kuyava et al. |
| 6,533,733 B1 | 3/2003 | Ericson et al. |
| 6,542,350 B1 | 4/2003 | Rogers |
| 6,558,321 B1 | 5/2003 | Burd et al. |
| 6,558,994 B2 | 5/2003 | Cha et al. |
| 6,573,563 B2 | 6/2003 | Lee et al. |
| 6,582,462 B1 | 6/2003 | Andersen et al. |
| 6,599,250 B2 | 7/2003 | Webb et al. |
| 6,605,112 B1 | 8/2003 | Moll et al. |
| 6,629,534 B1 | 10/2003 | St. Goar et al. |
| 6,640,137 B2 | 10/2003 | MacDonald |
| 6,641,610 B2 | 11/2003 | Wolf et al. |
| 6,645,143 B2 | 11/2003 | VanTassel et al. |
| 6,673,109 B2 | 1/2004 | Cox |
| 6,678,561 B2 | 1/2004 | Forsell et al. |
| 6,682,480 B1 | 1/2004 | Habib et al. |
| 6,682,503 B1 | 1/2004 | Fariss et al. |
| 6,682,559 B2 | 1/2004 | Myers et al. |
| 6,695,866 B1 | 2/2004 | Kuehn et al. |
| 6,709,385 B2 | 3/2004 | Forsell et al. |
| 6,718,200 B2 | 4/2004 | Marmaropoulos et al. |
| 6,719,787 B2 | 4/2004 | Cox |
| 6,719,788 B2 | 4/2004 | Cox |
| 6,719,789 B2 | 4/2004 | Cox |
| 6,731,976 B2 | 5/2004 | Penn et al. |
| 6,733,525 B2 | 5/2004 | Yang et al. |
| 6,736,846 B2 | 5/2004 | Cox |
| 6,752,813 B2 | 6/2004 | Goldfarb et al. |
| 6,796,942 B1 | 9/2004 | Kreiner et al. |
| 6,822,343 B2 | 11/2004 | Estevez |
| 6,851,628 B1 | 2/2005 | Garrison et al. |
| 6,855,115 B2 | 2/2005 | Fonseca et al. |
| 6,889,772 B2 | 5/2005 | Buytaert et al. |
| 6,890,300 B2 | 5/2005 | Lloyd et al. |
| 6,896,651 B2 | 5/2005 | Gross et al. |
| 6,896,690 B1 | 5/2005 | Lambrecht et al. |

| | | |
|---|---|---|
| 6,913,600 B2 | 7/2005 | Valley et al. |
| 6,915,165 B2 | 7/2005 | Forsell et al. |
| 6,926,246 B2 | 8/2005 | Ginggen et al. |
| 6,929,653 B2 | 8/2005 | Strecter |
| 6,932,792 B1 | 8/2005 | St. Goar et al. |
| 6,951,229 B2 | 10/2005 | Garrison et al. |
| 6,951,571 B1 | 10/2005 | Srivastava |
| 6,953,429 B2 | 10/2005 | Forsell et al. |
| 6,961,619 B2 | 11/2005 | Casey |
| 6,970,742 B2 | 11/2005 | Mann et al. |
| 6,979,350 B2 | 12/2005 | Moll et al. |
| 6,985,078 B2 | 1/2006 | Suzuki et al. |
| 6,989,027 B2 | 1/2006 | Allen et al. |
| 7,011,095 B2 | 3/2006 | Wolf et al. |
| 7,011,624 B2 | 3/2006 | Forsell et al. |
| 7,017,583 B2 | 3/2006 | Forsell et al. |
| 7,018,406 B2 | 3/2006 | Seguin et al. |
| 7,021,402 B2 | 4/2006 | Beato et al. |
| 7,025,727 B2 | 4/2006 | Brockway et al. |
| 7,044,920 B2 | 5/2006 | Letort et al. |
| 7,060,080 B2 | 6/2006 | Bachmann et al. |
| 7,081,683 B2 | 7/2006 | Ariav et al. |
| 7,109,933 B2 | 9/2006 | Ito et al. |
| 7,131,447 B2 | 11/2006 | Sterman et al. |
| 7,131,945 B2 | 11/2006 | Fink et al. |
| 7,134,580 B2 | 11/2006 | Garrison et al. |
| 7,144,400 B2 | 12/2006 | Byrum et al. |
| 7,147,640 B2 | 12/2006 | Huebner et al. |
| 7,153,262 B2 | 12/2006 | Stivoric et al. |
| 7,187,978 B2 | 3/2007 | Malek et al. |
| 7,225,032 B2 | 5/2007 | Schmeling et al. |
| 7,257,438 B2 | 8/2007 | Kinast |
| 7,285,090 B2 | 10/2007 | Stivoric et al. |
| 2001/0011543 A1 | 8/2001 | Forsell |
| 2001/0041823 A1 | 11/2001 | Snyder et al. |
| 2002/0049394 A1 | 4/2002 | Roy et al. |
| 2002/0120200 A1 | 8/2002 | Brockway et al. |
| 2002/0138009 A1 | 9/2002 | Brockway et al. |
| 2002/0177782 A1 | 11/2002 | Penner |
| 2003/0009201 A1 | 1/2003 | Forsell |
| 2003/0030893 A1 | 2/2003 | Cornelius et al. |
| 2003/0032857 A1 | 2/2003 | Forsell |
| 2003/0037591 A1 | 2/2003 | Ashton et al. |
| 2003/0045775 A1 | 3/2003 | Forsell |
| 2003/0066536 A1 | 4/2003 | Forsell |
| 2003/0088148 A1 | 5/2003 | Forsell |
| 2003/0092962 A1 | 5/2003 | Forsell |
| 2003/0093117 A1 | 5/2003 | Saadat |
| 2003/0100929 A1 | 5/2003 | Forsell |
| 2003/0105385 A1 | 6/2003 | Forsell |
| 2003/0109771 A1 | 6/2003 | Forsell |
| 2003/0114729 A1 | 6/2003 | Forsell |
| 2003/0125605 A1 | 7/2003 | Forsell |
| 2003/0125768 A1 | 7/2003 | Peter |
| 2003/0135089 A1 | 7/2003 | Forsell |
| 2003/0135090 A1 | 7/2003 | Forsell |
| 2003/0136417 A1 | 7/2003 | Fonseca et al. |
| 2003/0144648 A1 | 7/2003 | Forsell |
| 2003/0163079 A1 | 8/2003 | Burnett |
| 2003/0171787 A1* | 9/2003 | Money et al. .................. 607/57 |
| 2003/0216666 A1 | 11/2003 | Ericson et al. |
| 2004/0054352 A1 | 3/2004 | Adams et al. |
| 2004/0113790 A1 | 6/2004 | Hamel et al. |
| 2004/0133092 A1 | 7/2004 | Kain |
| 2004/0147969 A1 | 7/2004 | Mann et al. |
| 2004/0172087 A1 | 9/2004 | Forsell |
| 2004/0186396 A1 | 9/2004 | Roy et al. |
| 2004/0254537 A1 | 12/2004 | Conlon et al. |
| 2005/0015014 A1 | 1/2005 | Fonseca et al. |
| 2005/0025979 A1 | 2/2005 | Sandt et al. |
| 2005/0027175 A1 | 2/2005 | Yang |
| 2005/0038328 A1 | 2/2005 | Stoehrer et al. |
| 2005/0061079 A1 | 3/2005 | Schulman |
| 2005/0088352 A1* | 4/2005 | Parsche .................. 343/749 |
| 2005/0102026 A1 | 5/2005 | Turner et al. |
| 2005/0143766 A1* | 6/2005 | Bachmann et al. .................. 606/158 |
| 2005/0159789 A1 | 7/2005 | Brockway et al. |
| 2005/0165317 A1 | 7/2005 | Turner et al. |
| 2005/0182330 A1 | 8/2005 | Brockway et al. |
| 2005/0187482 A1 | 8/2005 | O'Brien et al. |
| 2005/0187488 A1 | 8/2005 | Wolf |
| 2005/0192642 A1 | 9/2005 | Forsell |
| 2005/0240155 A1 | 10/2005 | Conlon |
| 2005/0240156 A1 | 10/2005 | Conlon |
| 2005/0250979 A1 | 11/2005 | Coe |
| 2005/0267406 A1 | 12/2005 | Hassler |
| 2005/0267500 A1 | 12/2005 | Hassler et al. |
| 2005/0272968 A1 | 12/2005 | Byrum et al. |
| 2005/0277960 A1 | 12/2005 | Hassler et al. |
| 2005/0277974 A1 | 12/2005 | Hassler et al. |
| 2005/0288604 A1 | 12/2005 | Eigler et al. |
| 2005/0288720 A1 | 12/2005 | Ross et al. |
| 2005/0288721 A1 | 12/2005 | Girouard et al. |
| 2005/0288739 A1 | 12/2005 | Hassler et al. |
| 2005/0288740 A1 | 12/2005 | Hassler et al. |
| 2005/0288741 A1 | 12/2005 | Hassler et al. |
| 2005/0288742 A1 | 12/2005 | Giordano et al. |
| 2006/0002035 A1 | 1/2006 | Gao et al. |
| 2006/0010090 A1 | 1/2006 | Brockway et al. |
| 2006/0020224 A1 | 1/2006 | Geiger |
| 2006/0020305 A1 | 1/2006 | Desai et al. |
| 2006/0035446 A1 | 2/2006 | Chang et al. |
| 2006/0047205 A1 | 3/2006 | Ludomirsky et al. |
| 2006/0049714 A1 | 3/2006 | Liu et al. |
| 2006/0058627 A1 | 3/2006 | Flaherty et al. |
| 2006/0064134 A1 | 3/2006 | Mazar et al. |
| 2006/0085051 A1 | 4/2006 | Fritsch |
| 2006/0089571 A1 | 4/2006 | Gertner |
| 2006/0094966 A1 | 5/2006 | Brockway et al. |
| 2006/0100531 A1 | 5/2006 | Moser |
| 2006/0113187 A1 | 6/2006 | Deng et al. |
| 2006/0122285 A1 | 6/2006 | Falloon et al. |
| 2006/0122863 A1 | 6/2006 | Gottesman et al. |
| 2006/0142635 A1 | 6/2006 | Forsell |
| 2006/0149124 A1 | 7/2006 | Forsell |
| 2006/0149324 A1 | 7/2006 | Mann et al. |
| 2006/0149327 A1 | 7/2006 | Hedberg et al. |
| 2006/0157701 A1 | 7/2006 | Bauer et al. |
| 2006/0161186 A1 | 7/2006 | Hassler et al. |
| 2006/0173238 A1* | 8/2006 | Starkebaum .................. 600/37 |
| 2006/0178617 A1 | 8/2006 | Adams et al. |
| 2006/0178695 A1 | 8/2006 | Decant et al. |
| 2006/0183967 A1 | 8/2006 | Lechner |
| 2006/0184206 A1 | 8/2006 | Baker et al. |
| 2006/0189887 A1 | 8/2006 | Hassler et al. |
| 2006/0189888 A1 | 8/2006 | Hassler et al. |
| 2006/0189889 A1 | 8/2006 | Gertner |
| 2006/0199997 A1 | 9/2006 | Hassler et al. |
| 2006/0211912 A1 | 9/2006 | Dlugos et al. |
| 2006/0211913 A1 | 9/2006 | Dlugos et al. |
| 2006/0211914 A1 | 9/2006 | Hassler et al. |
| 2006/0217668 A1 | 9/2006 | Schulze et al. |
| 2006/0217673 A1 | 9/2006 | Schulze et al. |
| 2006/0235310 A1 | 10/2006 | O'Brien et al. |
| 2006/0235439 A1 | 10/2006 | Molitor et al. |
| 2006/0235448 A1 | 10/2006 | Roslin et al. |
| 2006/0244914 A1 | 11/2006 | Cech et al. |
| 2006/0247682 A1 | 11/2006 | Gerber et al. |
| 2006/0247719 A1 | 11/2006 | Maschino et al. |
| 2006/0247722 A1 | 11/2006 | Maschino et al. |
| 2006/0247723 A1 | 11/2006 | Gerber et al. |
| 2006/0247724 A1 | 11/2006 | Gerber et al. |
| 2006/0247725 A1 | 11/2006 | Gerber et al. |
| 2006/0252982 A1 | 11/2006 | Hassler et al. |
| 2006/0293625 A1 | 12/2006 | Hunt et al. |
| 2006/0293626 A1 | 12/2006 | Byrum et al. |
| 2006/0293627 A1 | 12/2006 | Byrum et al. |
| 2007/0010790 A1 | 1/2007 | Byrum et al. |
| 2007/0027356 A1 | 2/2007 | Ortiz |
| 2007/0027493 A1 | 2/2007 | Ben-Haim et al. |
| 2007/0067206 A1 | 3/2007 | Haggerty et al. |
| 2007/0070906 A1 | 3/2007 | Thakur |
| 2007/0072452 A1 | 3/2007 | Inagaki et al. |
| 2007/0081304 A1 | 4/2007 | Takeguchi |
| 2007/0156013 A1 | 7/2007 | Birk |
| 2007/0167672 A1 | 7/2007 | Dlugos et al. |
| 2007/0173881 A1 | 7/2007 | Birk et al. |
| 2007/0179583 A1 | 8/2007 | Goetzinger et al. |

| | | | |
|---|---|---|---|
| 2007/0208313 A1 | 9/2007 | Conlon et al. | |
| 2007/0225781 A1 | 9/2007 | Saadat et al. | |
| 2008/0009680 A1 | 1/2008 | Hassler | |
| 2008/0275478 A1* | 11/2008 | Buffard et al. | 606/151 |
| 2008/0287776 A1* | 11/2008 | Ephrath et al. | 600/424 |

FOREIGN PATENT DOCUMENTS

| | | |
|---|---|---|
| CA | 1119469 | 3/1982 |
| CA | 1275135 | 10/1990 |
| CA | 1277885 | 12/1990 |
| CA | 1317482 | 5/1993 |
| CA | 2082015 | 5/1993 |
| CA | 1327191 | 2/1994 |
| CA | 2119101 | 9/1994 |
| CA | 2305998 | 4/1999 |
| CN | 1119469 | 3/1996 |
| CN | 1241003 | 1/2000 |
| EA | 4581 | 6/2004 |
| EP | 125387 B1 | 2/1984 |
| EP | 417171 | 3/1991 |
| EP | 508141 | 10/1992 |
| EP | 568730 | 11/1993 |
| EP | 605302 | 7/1994 |
| EP | 660482 | 6/1995 |
| EP | 714017 | 5/1996 |
| EP | 769340 | 4/1997 |
| EP | 846475 | 6/1998 |
| EP | 848780 | 6/1998 |
| EP | 876808 | 11/1998 |
| EP | 888079 | 1/1999 |
| EP | 914059 | 5/1999 |
| EP | 981293 | 3/2000 |
| EP | 997680 | 5/2000 |
| EP | 1003021 | 5/2000 |
| EP | 1022983 | 8/2000 |
| EP | 1050265 | 11/2000 |
| EP | 1115329 | 7/2001 |
| EP | 1119314 | 8/2001 |
| EP | 1128871 | 9/2001 |
| EP | 1202674 | 5/2002 |
| EP | 1213991 | 6/2002 |
| EP | 1253877 | 11/2002 |
| EP | 1253879 | 11/2002 |
| EP | 1253880 | 11/2002 |
| EP | 1253881 | 11/2002 |
| EP | 1253883 | 11/2002 |
| EP | 1253888 | 11/2002 |
| EP | 1255511 | 11/2002 |
| EP | 1255513 | 11/2002 |
| EP | 1255514 | 11/2002 |
| EP | 1263355 | 12/2002 |
| EP | 1263357 | 12/2002 |
| EP | 1284691 | 2/2003 |
| EP | 1374758 | 1/2004 |
| EP | 1488735 | 12/2004 |
| EP | 1500411 | 1/2005 |
| EP | 1510306 | 3/2005 |
| EP | 1518514 | 3/2005 |
| EP | 1547549 | 6/2005 |
| EP | 1563814 | 8/2005 |
| EP | 1568338 | 8/2005 |
| EP | 1582175 | 10/2005 |
| EP | 1582176 | 10/2005 |
| EP | 1584303 | 10/2005 |
| EP | 1586283 | 10/2005 |
| EP | 1591086 | 11/2005 |
| EP | 1593359 | 11/2005 |
| EP | 1598030 | 11/2005 |
| EP | 1609440 | 12/2005 |
| EP | 1674033 | 6/2006 |
| EP | 1736123 | 12/2006 |
| EP | 1799119 | 6/2007 |
| GB | 2355937 | 5/2001 |
| WO | WO-8911244 | 11/1989 |
| WO | WO-8911701 | 11/1989 |
| WO | WO-9004368 | 5/1990 |
| WO | WO-9511057 | 4/1995 |
| WO | WO-9715351 | 5/1997 |
| WO | WO-9733513 | 9/1997 |
| WO | WO-9833554 | 8/1998 |
| WO | WO-9835610 | 8/1998 |
| WO | WO-9901063 | 1/1999 |
| WO | WO-9918850 | 4/1999 |
| WO | WO-0004945 | 2/2000 |
| WO | WO-0033738 | 6/2000 |
| WO | WO-0072899 | 12/2000 |
| WO | WO-0104487 | 1/2001 |
| WO | WO-0112075 | 2/2001 |
| WO | WO-0112076 | 2/2001 |
| WO | WO-0112077 | 2/2001 |
| WO | WO-0112078 | 2/2001 |
| WO | WO-0121066 | 3/2001 |
| WO | WO-0136014 | 5/2001 |
| WO | WO-0145485 | 6/2001 |
| WO | WO-0145486 | 6/2001 |
| WO | WO-0147431 | 7/2001 |
| WO | WO-0147432 | 7/2001 |
| WO | WO-0147433 | 7/2001 |
| WO | WO-0147434 | 7/2001 |
| WO | WO-0147435 | 7/2001 |
| WO | WO-0147440 | 7/2001 |
| WO | WO-0147575 | 7/2001 |
| WO | WO-0148451 | 7/2001 |
| WO | WO-0149245 | 7/2001 |
| WO | WO-0150832 | 7/2001 |
| WO | WO-0150833 | 7/2001 |
| WO | WO-0154626 | 8/2001 |
| WO | WO-0158388 | 8/2001 |
| WO | WO-0158390 | 8/2001 |
| WO | WO-0158391 | 8/2001 |
| WO | WO-0158393 | 8/2001 |
| WO | WO-0160453 | 8/2001 |
| WO | WO-0181890 | 11/2001 |
| WO | WO-0200118 | 1/2002 |
| WO | WO-0215769 | 2/2002 |
| WO | WO-0226161 | 4/2002 |
| WO | WO-02053228 | 7/2002 |
| WO | WO-02055126 | 7/2002 |
| WO | WO-02058551 | 8/2002 |
| WO | WO-02065894 | 8/2002 |
| WO | WO-02076289 | 10/2002 |
| WO | WO-02082984 | 10/2002 |
| WO | WO-02089655 | 11/2002 |
| WO | WO-02090894 | 11/2002 |
| WO | WO-02100481 | 12/2002 |
| WO | WO-03002192 | 1/2003 |
| WO | WO-03002193 | 1/2003 |
| WO | WO-03020182 | 3/2003 |
| WO | WO-03061467 | 7/2003 |
| WO | WO-03061504 | 7/2003 |
| WO | WO-03096889 | 11/2003 |
| WO | WO-2004014456 | 2/2004 |
| WO | WO-2004019773 | 3/2004 |
| WO | WO-2004058101 | 7/2004 |
| WO | WO-2004066879 | 8/2004 |
| WO | WO-2004110263 | 12/2004 |
| WO | WO-2005000206 | 1/2005 |
| WO | WO-2005007075 | 1/2005 |
| WO | WO-2005107583 | 11/2005 |
| WO | WO-2006001851 | 1/2006 |
| WO | WO-2006035446 | 4/2006 |
| WO | WO-2006113187 | 10/2006 |
| WO | WO-2006122285 | 11/2006 |
| WO | WO-2007067206 | 6/2007 |
| WO | WO-2007070906 | 6/2007 |
| WO | WO-20070072452 | 6/2007 |
| WO | WO-2007081304 | 7/2007 |
| WO | WO-2007104356 | 9/2007 |

OTHER PUBLICATIONS

"Rad Hard Aerospace Components Products", Honeywell product and service information from website http://www.honeywell.com/sites/portal?smap=aerospace&page=Radiation-Hardened-Electronics3&theme=T6&catID=C815147E4-8786-29FE-49EB-C21C8790AA99&id=H0166BA51-5344-E57E-5C37-C6333EA43F61&sel=1; 1 page.

"Radiation Hardened Electronics and Radiation Technology", Honeywell product and service information from website http://www.honeywell.com/sites/portal?smap=aerospace&p.=Radiation-Hardened-Electronics&theme=T4; 2 pages.

Kirchner, G., "Honeywell and Synopsys: Concept-to-Parts Solutions for Next Generation Rad-Hard ASICs", in online magazine Compiler, http://www.synopsys.com/news/pubs/compiler/artlead_redasic-apr05.html, Apr. 2005, 5 pages.

P.A. Neukomm and H. Kundig, "Passive Wireless Actuator Control and Sensor Signal Transmission," Sensors and Actuators, A21-A23 (1990) 258-262.

* cited by examiner

SYSTEM AND METHOD OF ALIGNING AN IMPLANTABLE ANTENNA

FIELD

The present disclosure relates to methods and systems for predictably and reliably aligning an implantable antenna with an external reader thereby facilitating power coupling and/or data transfer therebetween.

BACKGROUND

Obesity is becoming a growing concern, particularly in the United States, as the number of obese people continues to increase, and more is learned about the negative health effects of obesity. Morbid obesity, in which a person is 100 pounds or more over ideal body weight, in particular poses significant risks for severe health problems. Accordingly, a great deal of attention is being focused on treating obese patients. One method of treating morbid obesity has been to place a restriction device, such as an elongated band, about the upper portion of the stomach. Gastric bands have typically comprised a fluid-filled elastomeric balloon with fixed endpoints that encircles the stomach just inferior to the esophageal-gastric junction to form a small gastric pouch above the band and a reduced stoma opening in the stomach. When fluid is infused into the balloon, the band expands against the stomach creating a food intake restriction or stoma in the stomach. To decrease this restriction, fluid is removed from the band. The effect of the band is to reduce the available stomach volume and thus the amount of food that can be consumed before becoming "full."

Food restriction devices have also comprised mechanically adjusted bands that similarly encircle the upper portion of the stomach. These bands include any number of resilient materials or gearing devices, as well as drive members, for adjusting the bands. Additionally, gastric bands have been developed that include both hydraulic and mechanical drive elements. It is also known to restrict the available food volume in the stomach cavity by implanting an inflatable elastomeric balloon within the stomach cavity itself. The balloon is filled with a fluid to expand against the stomach walls and, thereby, decrease the available food volume within the stomach.

With each of the above-described food restriction devices, safe, effective treatment requires that the device be regularly monitored and adjusted to vary the degree of restriction applied to the stomach. Traditionally, adjusting a gastric band required a scheduled clinician visit during which a hypodermic needle and syringe were used to permeate the patient's skin and remove fluid from the balloon. More recently, implantable pumps have been developed which enable non-invasive adjustments of the band. An external programmer communicates with the implanted pump using telemetry to control the pump. During a scheduled visit, a physician places a hand-held portion of the programmer near the gastric implant and transmits command signals to the implant. The implant in turn adjusts the band and transmits a response command to the programmer.

Implants such as those described above include electronics which require a power source that is sufficient for the intended function, such as making adjustments to the gastric band. Such devices may be internally powered by a battery or capacitor while others may be powered by an externally coupled power source or passive telemetry system. When coupling externally, the efficiencies between the implant and external device diminish substantially as the distance between them increases. There can also be significant power losses through tissue. Additionally, it can be difficult and time-consuming to properly align an internal antenna with an external reader so as to power the implant and/or transmit data therebetween.

Thus, there remains a need for a system and method capable of facilitating power coupling and/or data transfer between an implantable antenna and an external device.

SUMMARY

Various aspects of an implantable restriction system are provided herein. In one such aspect the system includes an implantable restriction device configured to form a restriction in a pathway. The system can also include an implantable housing (e.g., a sensor housing) and an implantable antenna movably coupled to the housing such that the antenna can align with an external device for communicating therewith. The antenna can be effective to communicate with the external device to transcutaneously deliver energy to power the device to the antenna. The antenna can also be effective communicate (e.g., transmit and/or receive) various types of data to/from an external device.

As described below, the antenna can be movable in response to variety of factors. For example, the antenna can be movable in response to at least one of manual manipulation, a magnetic force, an electromagnetic force, a gravitational force, and a buoyant force. To facilitate such movement, the system can include at least one magnetic element coupled to the antenna wherein the at least one magnetic element is configured to align with an external magnetic member. Also, the antenna can contain an element (e.g., a weight) effective to enable a gravitational force to align the antenna in a desired orientation. In such an example, the antenna can be substantially ring-shaped and the weight can be positioned below and substantially along a central axis of the antenna. Also, the housing can be at least a portion of a gimbal element such that the antenna is free to rotate about a first axis and the antenna is also free to rotate about a second axis wherein the first axis can be substantially orthogonal to the second axis.

The system can also include an implantable sensor configured to measure at least one of an operational value of a system parameter and a value of a physiological parameter. In use, the antenna can be effective to communicate the operational value or the physiological value to the external device. For example, the implantable sensor can be a pressure sensor.

The antenna can be disposed on or coupled to various forms of a housing. For example, the antenna can be disposed on a sensor housing that is movably mounted to a base housing that is configured to engage an anatomical location (e.g., the fascia). In such an example, the antenna can be statically mounted upon the sensor housing, and the housing can be movably mounted to the base housing (e.g., by way of a ball and socket joint).

In another aspect, an implantable restriction system is provided which includes an implantable gastric restriction device configured to form a restriction in a patient. The system can also include an implantable sensor configured to measure at least one of a value of a system parameter and a physiological parameter. Additionally, the system can include an implantable antenna in communication with the implantable sensor wherein the implantable antenna can be configured to communicate with an external device and can be capable of achieving an effective orientation to enable the antenna to communicate with the external device. In this aspect, the antenna can be movable to the effective orientation in response to at least one of manual manipulation, a magnetic force, an electromagnetic force, and a gravitational force.

The antenna can be configured to be movable to the effective orientation in various manners. For example, the antenna can be movably coupled to a housing. In such an example, the antenna can be statically mounted to a housing which in turn can be movably mated to a base housing. The implantable antenna can also be coupled to a housing wherein the housing is at least a portion of a gimbal element such that the antenna is free to rotate about a first axis and the antenna is also free to rotate about a second axis wherein the first axis being substantially orthogonal to the second axis.

Additionally, various methods for transcutaneously communicating with an implantable restriction system are provided. In one such aspect, the method includes implanting a restriction system within a patient wherein the system includes a device effective to form a restriction in a pathway and an antenna effective to communicate with an external device to receive and transmit at least one of energy and data. The method can also include enabling the antenna to be movable with respect to at least a portion of a housing such that the antenna can align with the external device for communicating therewith. For example, the antenna can align with the external device in a desired orientation in response to at least one of manual manipulation, a magnetic force, an electromagnetic force, and a gravitational force.

BRIEF DESCRIPTION OF THE DRAWINGS

The present disclosure will be more fully understood from the following detailed description taken in conjunction with the accompanying drawings, in which.

DETAILED DESCRIPTION

Figure 1A:
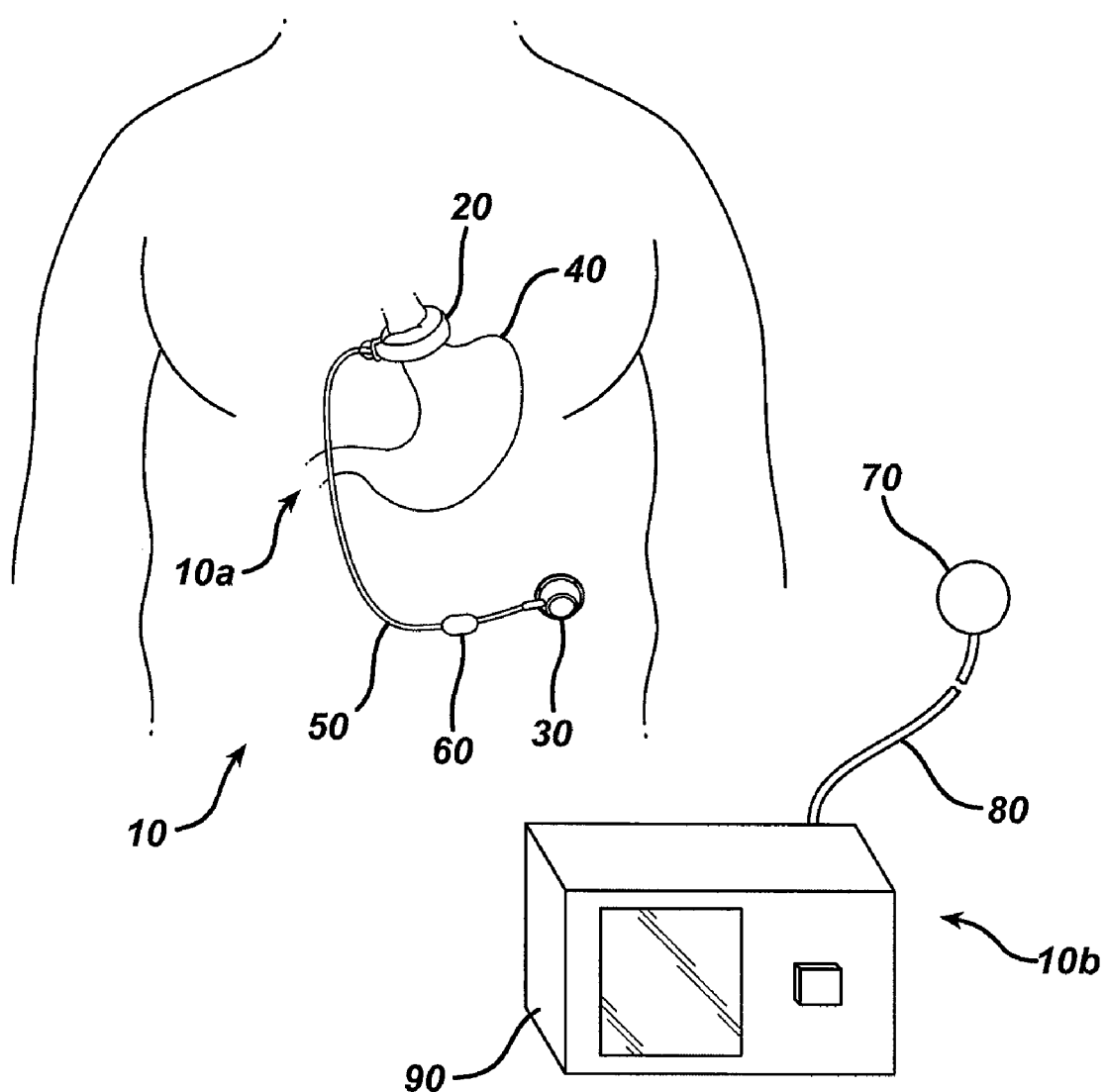
FIG. 1A is a schematic diagram of an embodiment of a food intake restriction system.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Systems and methods for communicating with an implantable restriction system are provided herein. In general, the implantable restriction system includes some type of internal antenna which may be coupled to or in communication with an implantable sensor configured to measure one or more operational parameter (e.g., pressure) and/or one or more physiological parameter. In use, the antenna can be any type of antenna capable of coupling with an external antenna so as to allow the implantable system to be powered and/or capable of transferring and/or receiving data (e.g., pressure readings) therebetween.

To facilitate such coupling and/or communication, the system and antenna can be configured in various manners so that it is able to attain and maintain proper alignment. For example, the antenna can be coupled to a housing, or a portion of a housing such that the antenna can move relative to the housing or the portion of the housing. In one embodiment the antenna can be coupled to a gimbal element so as to allow the antenna to freely swivel, move, and/or rotate about at least a first axis and a second axis wherein the first axis and the second axis are orthogonal to one another. In other embodiments, the antenna can be coupled to and/or include a weight or a weighted portion. In such an embodiment, the alignment of the antenna position can be known and easily reproduced by placing the patient in a certain orientation (e.g., standing). In other embodiments, the antenna can be in communication with (e.g., coupled to) at least one magnetic element configured to align with an external magnet thereby aligning the antenna with an external antenna or reader. In yet another embodiment, the antenna can be disposed on an implantable housing which in turn can be movably mounted to a base housing (e.g., via a ball and socket mounting) such that the antenna is free to move relative to the base housing while the base housing can be secured to an anatomical location (e.g., sutured to tissue). Thus, the presently disclosed embodiments provide a reliable system and method for facilitating power coupling and/or data transfer between the implantable system and an external reader.

Providing a movable antenna can facilitate coupling with an external device for various reasons. Given the relatively small size of the implant, any such antenna will typically exhibit low performance due to the physics of antenna coupling to the media (i.e. body tissues, air, etc.). Larger antennae, if designed correctly, will couple better than smaller antennae, and if the antenna cannot be a sizable fraction of the wavelength it will perform more like a probe than an antenna, exhibiting low gain and requiring higher power for transmit and more receiver gain in order to compensate. One skilled in the art would appreciate that antennae must occupy the space of at least about ¼ and more ideally about ½ of a wavelength to perform in an efficient manner. Since $c=f\lambda$ where c=speed of electromagnetic propagation in a given media, f is frequency and λ is the wavelength, it can be seen that at frequencies other than microwave, associating an antenna design in an implant that is a sizable fraction of the wavelength is impractical. If, say, the communication frequency is in one of the industrial, scientific, and medical ("ISM") radio bands that is conducive for transmission through tissue (approximately 13 MHz) a ¼ wavelength antenna element would be about 3.8 m long. Therefore certain compromises need to be made in order to provide efficient coupling of transmissions to and from the implant in a practical implant size. Thus, as described, the antenna can be constructed to be part of an entire implanted device (e.g., a restricting band, connecting tube, port, etc.) in order to increase its relative size and approach an ideal size. Additionally, polarization of the antenna system can also affect the coupling, with approximately 20 dB of attenuation occurring if the elements of the system are not properly aligned. Circularly polarized antennae can be used but are best exploited if the antenna system is of an optimal size. Therefore, it is an advantage to have a movable antenna in the implant in order to optimally couple the antenna system.

Figure 1B:
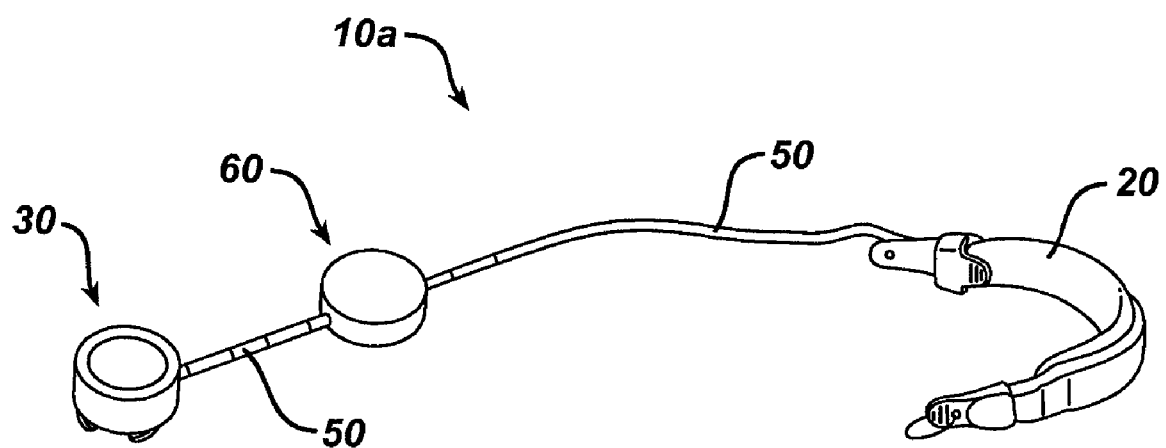
FIG. 1B is perspective view of an embodiment of an implantable portion of the food intake restriction system of FIG. 1A.

While the present disclosure can be used with a variety of restriction systems known in the art, FIG. 1A illustrates one exemplary embodiment of a food intake restriction system 10 in use in a patient. As shown, the system 10 generally includes an implantable portion 10a and an external portion 10b. FIG. 1B illustrates the implantable portion 10a outside of a patient. As shown, the implantable portion 10a includes an adjustable gastric band 20 that is configured to be positioned around the upper portion of a patient's stomach 40 and an injection port housing 30 that is fluidly coupled to the adjustable gastric band 20, e.g., via a catheter 50. The injection port 30 is configured to allow fluid to be introduced into and removed from the gastric band 20 to thereby adjust the size of the band 20 and thus the pressure applied to the stomach 40. The injection port 30 can thus be implanted at a location within the body that is accessible through tissue. Typically, injection ports are positioned in the lateral subcostal region of the patient's abdomen under the skin and layers of fatty tissue. Surgeons also typically implant injection ports on the sternum of the patient.

The internal portion 10a can also include a sensing or measuring device that is in fluid communication with the closed fluid circuit in the implantable portion 10a. In one embodiment, the sensing device is a pressure sensing device configured to measure the fluid pressure of the closed fluid circuit. While the pressure measuring device can have various configurations and can be positioned anywhere along the internal portion 10a, including within the injection port 30 and as described further below, in the illustrated embodiment the pressure measuring device is in the form of a pressure sensor that is disposed within a sensor housing 60 positioned adjacent to the injection port 30. The catheter 50 can include a first portion that is coupled between the gastric band 20 and the pressure sensor housing 60 and a second portion that is coupled between the pressure sensor housing 60 and the injection port 30. While it is understood that the sensing device can be configured to obtain data relating to one or more relevant parameters, generally it will be described herein in a context of a pressure sensing device.

As further shown in FIG. 1A, the external portion 10b generally includes a data reading device 70 that is configured to be positioned on the skin surface above the pressure sensor housing 60 (which can be implanted beneath thick tissue, e.g., over 10 cm thick) to non-invasively communicate (as described in detail below) with the pressure sensor housing 60 and thereby obtain pressure measurements. The data reading device 70 can optionally be electrically coupled (wirelessly or wired, as in this embodiment via an electrical cable assembly 80) to a control box 90 that can display the pressure measurements, other data obtained from the data reading device 70, and/or data alerts. While shown in this example as being local to the patient, the control box 90 can be at a location local to or remote from the patient.

Figure 2A:
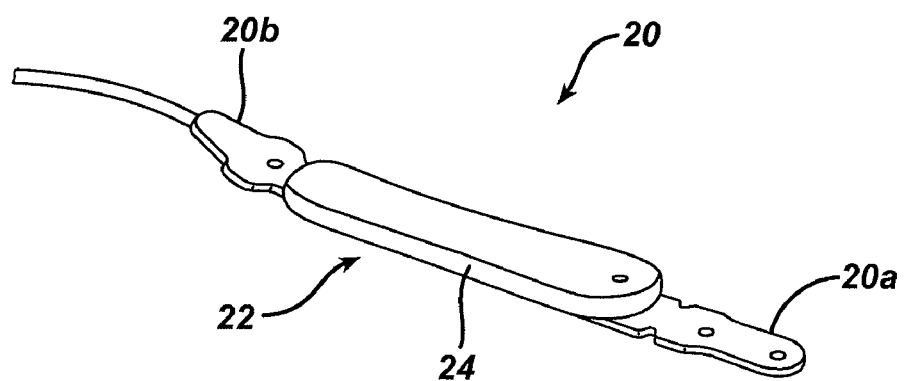
FIG. 2A is a perspective view of the food intake restriction device of FIG. 1A.

FIG. 2A shows the gastric band 20 in more detail. While the gastric band 20 can have a variety of configurations, and various gastric bands currently known in the art can be used with the present disclosure, in the illustrated embodiment the gastric band 20 has a generally elongate shape with a support structure 22 having first and second opposite ends 20a, 20b that can be formed in a loop such that the ends are secured to each other. Various mating techniques can be used to secure the ends 20a, 20b to one another. In the illustrated embodiment, the ends 20a, 20b are in the form of straps that mate together, with one laying on top of the other. In another embodiment, illustrated, for example, in FIGS. 1B and 2B, a support structure at one end of the gastric band 20 can include an opening through which the other end of the gastric band 20 can feed through to secure the ends to one another. The gastric band 20 can also include a variable volume member, such as an inflatable balloon 24, that is disposed or formed on one side of the support structure 22 and that is configured to be positioned adjacent to tissue. The balloon 24 can expand or contract against the outer wall of the stomach to form an adjustable stoma for controllably restricting food intake into the stomach.

A person skilled in the art will appreciate that the gastric band can have a variety of other configurations. Moreover, the various methods and devices disclosed herein have equal applicability to other types of implantable bands. For example, bands are used for the treatment of fecal incontinence, as described in U.S. Pat. No. 6,461,292 which is hereby incorporated by reference. Bands can also be used to treat urinary incontinence, as described in U.S. Publication No. 2003/0105385 which is hereby incorporated by reference. Bands can also be used to treat heartburn and/or acid reflux, as disclosed in U.S. Pat. No. 6,470,892 which is hereby incorporated by reference. Bands can also be used to treat impotence, as described in U.S. Publication No. 2003/0114729 which is hereby incorporated by reference.

Figure 2B:
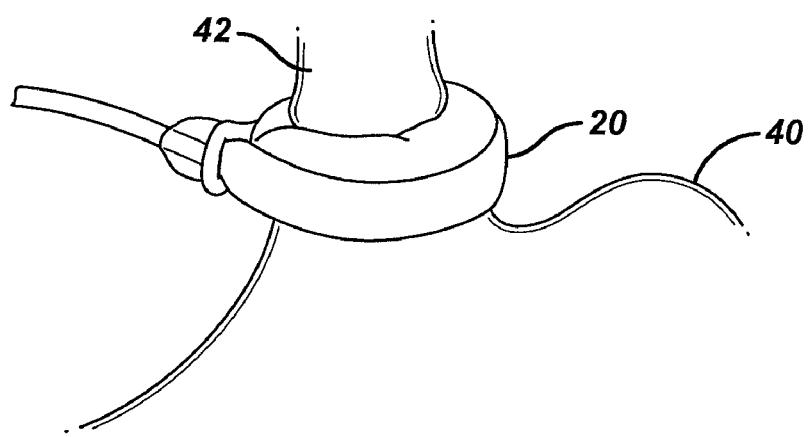
FIG. 2B is a schematic diagram of the food intake restriction device of FIG. 2A applied about the gastro-esophageal junction of a patient.

FIG. 2B shows the adjustable gastric band 20 applied about the gastro-esophageal junction of a patient. As shown, the band 20 at least substantially encloses the upper portion of the stomach 40 near the junction with the patient's esophagus 42. After the band 20 is implanted, preferably in the deflated configuration wherein the band 20 contains little or no fluid, the band 20 can be inflated, e.g., using saline, to decrease the size of the stoma opening. A person skilled in the art will appreciate that various techniques, including mechanical and electrical techniques, can be used to adjust the band 20. FIG. 2B also shows an alternate location of a sensing device 41, disposed in a buckle 43 of the band 20.

Figure 3:
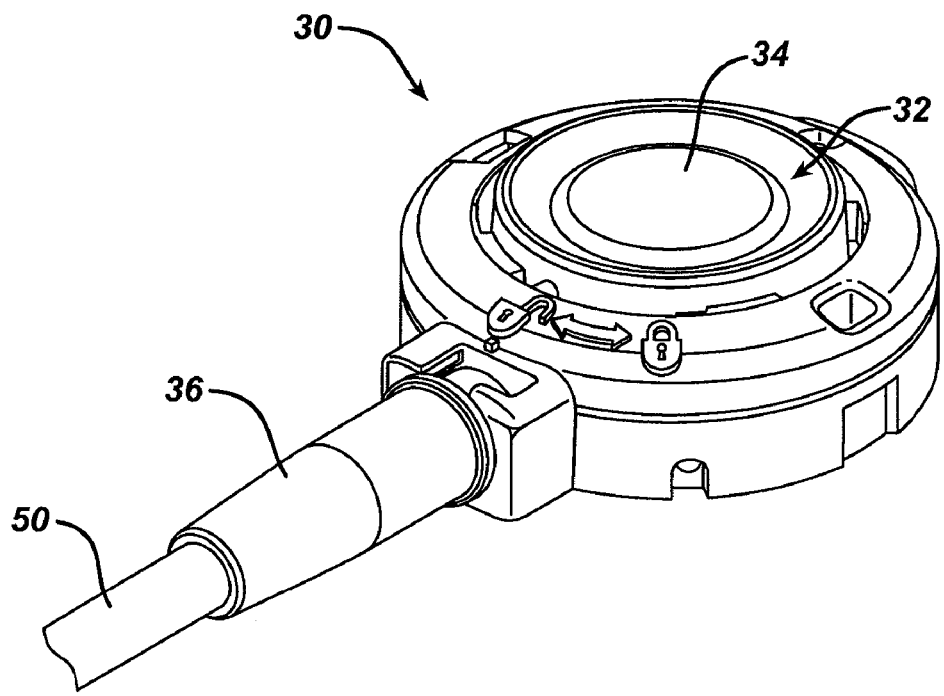
FIG. 3 is a perspective view of an embodiment of the injection port housing of FIG. 1A.

The fluid injection port 30 can also have a variety of configurations. In the embodiment shown in FIG. 3, the injection port 30 has a generally cylindrical housing with a distal or bottom surface and a perimeter wall extending proximally from the bottom surface and defining a proximal opening 32. The proximal opening 32 can include a needle-penetrable septum 34 extending there across and providing access to a fluid reservoir (not visible in FIG. 3) formed within the housing. The septum 34 is preferably placed in a proximal enough position such that the depth of the reservoir is sufficient enough to expose the open tip of a needle, such as a Huber needle, so that fluid transfer can take place. The septum 34 is preferably arranged so that it will self seal after being punctured by a needle and the needle is withdrawn. As further shown in FIG. 3, the port 30 can further include a catheter tube connection member 36 that is in fluid communication with the reservoir and that is configured to couple to a catheter (e.g., the catheter 50). A person skilled in the art will appreciate that the housing can be made from any number of materials, including stainless steel, titanium, or polymeric materials, and the septum 34 can likewise be made from any number of materials, including silicone.

The reading device 70 can also have a variety of configurations, and one exemplary pressure reading device is disclosed in more detail in commonly-owned U.S. Publication No. 2006/0189888 and U.S. Publication No. 2006/0199997, which are hereby incorporated by reference. In general, the reading device 70 can non-invasively measure the pressure of the fluid within the implanted portion 10a even when the pressure sensing device is implanted beneath thick (at least over 10 cm) subcutaneous fat tissue. The physician can hold the reading device 70 against the patient's skin near the location of the sensor housing 60 and/or other pressure sensing device location(s), obtain sensed pressure data and possibly other information as discussed herein, and observe the pressure reading (and/or other data) on a display on the control box 90. The data reading device 70 can also be removably attached to the patient, as discussed further below, such as during a prolonged examination, using straps, adhesives, and other well-known methods. The data reading device 70 can operate through conventional cloth or paper surgical drapes, and can also include a disposal cover (not shown) that may be replaced for each patient.

Figure 4:
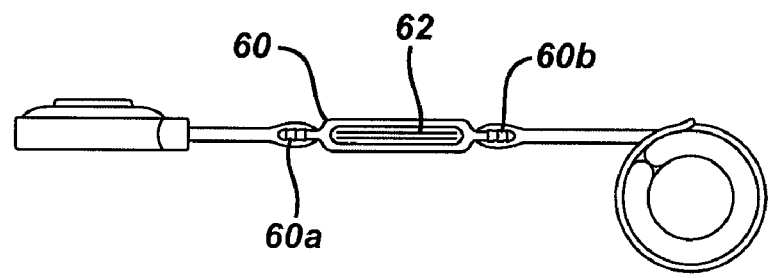
FIG. 4 is a perspective view of an embodiment of the sensor housing of FIG. 1A.

As indicated above, the system 10 can also include one or more sensors for monitoring the operation of the gastric restriction system 10. The sensor(s) can be configured to measure various operational parameters of the system 10 including, but not limited to, a pressure within the system, a temperature within the system, a peristaltic pulse event or frequency, the peristaltic pulse width, the peristaltic pulse duration, and the peristaltic pulse amplitude. In one exemplary embodiment, the system can include a sensor in the form of a pressure measuring device that is in communication with the closed fluid circuit and that is configured to measure the fluid pressure within the system, which corresponds to the amount of restriction applied by the adjustable gastric band to the patient's stomach. In use, measuring the fluid pressure, or any other control parameter of the system, can enable a physician to evaluate the performance of the restriction system. In the illustrated embodiment, shown in FIG. 4, the pressure measuring device is in the form of a pressure sensor 62 disposed within the sensor housing 60. The pressure measuring device can, however, be disposed anywhere within the closed hydraulic circuit of the implantable portion, and various exemplary locations and configurations are disclosed in more detail in commonly-owned U.S. Publication No. 2006/0211913 entitled "Non-Invasive Pressure Measurement In a Fluid Adjustable Restrictive Device," filed on Mar. 7, 2006 and hereby incorporated by reference. In general, the illustrated sensor housing 60 includes an inlet 60a and an outlet 60b that are in fluid communication with the fluid in the implantable portion 10a. An already-implanted catheter 50 can be retrofitted with the sensor housing 60, such as by severing the catheter 50 and inserting barbed connectors (or any other connectors, such as clamps, clips, adhesives, welding, etc.) into the severed ends of the catheter 50. The sensor 62 can be disposed within the housing 60 and be configured to respond to fluid pressure changes within the hydraulic circuit and convert the pressure changes into a usable form of data.

Various pressure sensors known in the art can be used as the pressure sensor 62, such as a wireless pressure sensor provided by CardioMEMS, Inc. of Atlanta, Ga., though a suitable Micro-Electro-Mechanical Systems ("MEMS") pressure sensor may be obtained from any other source, including but not limited to Integrated Sensing Systems, Inc. (ISSYS) of Ypsilanti, Mich. and Remon Medical Technologies, Inc. of Waltham, Mass. One exemplary MEMS pressure sensor is described in U.S. Pat. No. 6,855,115, the disclosure of which is incorporated by reference herein for illustrative purposes only. It will also be appreciated by a person skilled in the art that suitable pressure sensors can include, but are not limited to, capacitive, piezoresistive, silicon strain gauge, or ultrasonic (acoustic) pressure sensors, as well as various other devices capable of measuring pressure.

Figure 5:
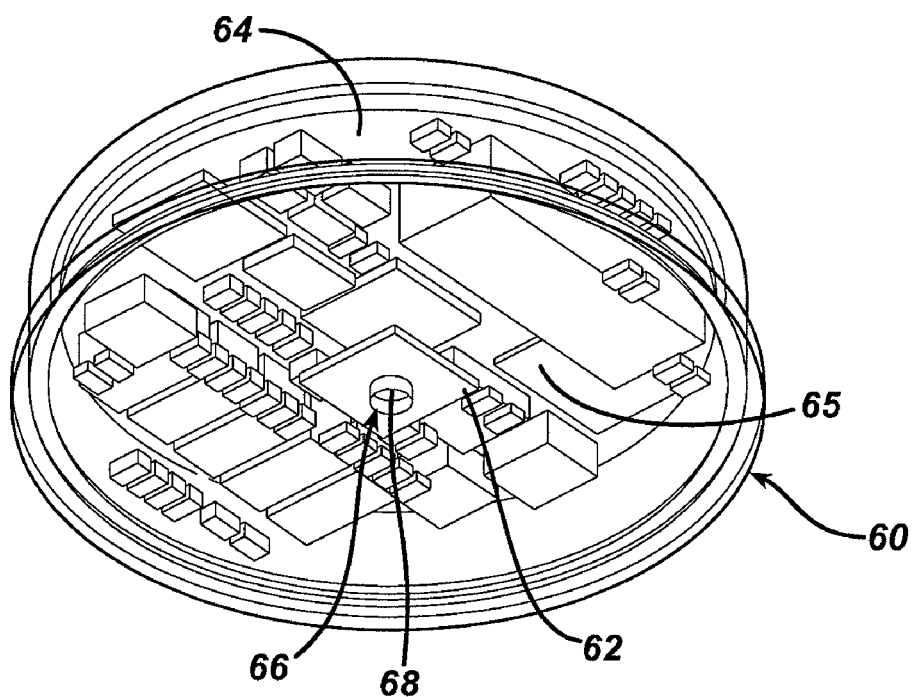
FIG. 5 illustrates an embodiment of the sensor housing of FIG. 1A.

One embodiment of a configuration of the sensor housing 60 having the sensor 62 disposed within it is shown in FIG. 5. The sensor housing 60 in this example includes a motherboard that can serve as a hermetic container to prevent fluid from contacting any elements disposed within the sensor housing 60, except as discussed for the sensor 62. The sensor housing 60 can be made from any biocompatible material appropriate for use in a body, such as a polymer, biocompatible metal, and other similar types of material. Furthermore, the sensor housing 60 can be made from any one or more of transparent (as shown in FIG. 5), opaque, semi-opaque, and radio-opaque materials. A circuit board 64 including, among other elements, a microcontroller 65 (e.g., a processor), can also be disposed within the housing 60 to help process and communicate pressure measurements gathered by the sensor 62, and also possibly other data related to the band 20. As further discussed below, the circuit board 64 can also include a transcutaneous energy transfer (TET)/telemetry coil and a capacitor. Optionally, a temperature sensor can be integrated into the circuit board 64. The microcontroller 65, the TET/telemetry coil, the capacitor, and/or the temperature sensor can be in communication via the circuit board 64 or via any other suitable component(s). As described below, the TET/telemetry coil and capacitor can collectively form a tuned tank circuit for receiving power from the external portion 10b and transmitting pressure measurements to a pressure reading device, e.g., the reading device 70. Moreover, to the extent that a telemetry component associated with the pressure sensor 62 is unable to reach a telemetry device external to the patient without some assistance, such assistance can be provided by any suitable number of relays (not shown) or other devices.

In use, fluid can enter the sensor housing 60 through an opening 66 located anywhere on the housing's surface (here, the bottom surface) and come into contact with a pressure sensing surface 68 of the sensor 62. The sensor 62 is typically hermetically sealed to the motherboard such that fluid entering the opening 66 cannot infiltrate and affect operation of the sensor 62 except at the pressure sensing surface 68. The sensor 62 can measure the pressure of fluid coming into contact with the pressure sensing surface 68 as fluid flows in and out of the opening 66. For example, the pressure sensing surface 68 can include a diaphragm having a deformable surface such that when fluid flows through the opening 66, the fluid impacts the surface of the diaphragm, causing the surface to mechanically displace. The mechanical displacement of the diaphragm can be converted to an electrical signal by a variable resistance circuit including a pair of variable resistance, silicon strain gauges. One strain gauge can be attached to a center portion of diaphragm to measure the displacement of the diaphragm, while the second, matched strain gauge can be attached near the outer edge of diaphragm. The strain gauges can be attached to the diaphragm with adhesives or can be diffused into the diaphragm structure. As fluid pressure within band 20 fluctuates, the surface of the diaphragm can deform up or down, thereby producing a resistance change in the center strain gauge.

Figure 6:
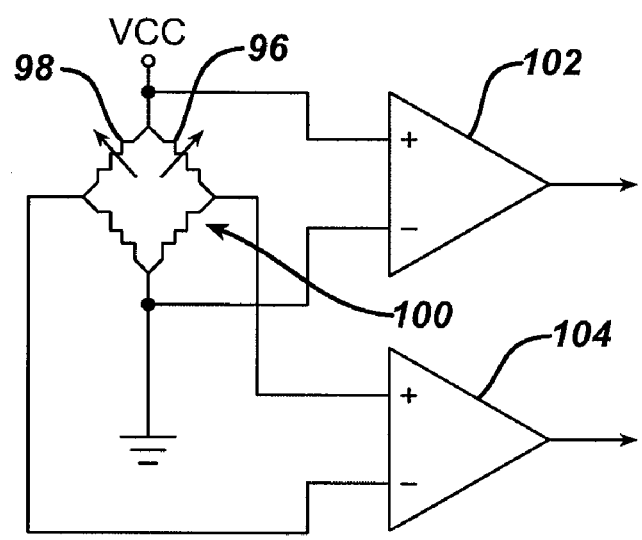
FIG. 6 is a schematic of an embodiment of a variable resistance circuit for the sensor of FIG. 5.

One embodiment of a variable resistance circuit for the sensor 62 is shown in FIG. 6. The circuit includes first and second strain gauges 96, 98 that form the top two resistance elements of a half-compensated, Wheatstone bridge circuit 100. As the first strain gauge 96 reacts to the mechanical displacements of the sensor's diaphragm, the changing resistance of the first gauge 96 changes the potential across the top portion of the bridge circuit 100. The second strain gauge 98 is matched to the first strain gauge 96 and athermalizes the Wheatstone bridge circuit 100. First and second differential amplifiers 102, 104 are connected to the bridge circuit 100 to measure the change in potential within the bridge circuit 100 due to the variable resistance strain gauges 96, 98. In particular, the first differential amplifier 102 measures the voltage across the entire bridge circuit 100, while the second differential amplifier 104 measures the differential voltage across the strain gauge half of bridge circuit 100. The greater the differential between the strain gauge voltages, for a fixed voltage across the bridge, the greater the pressure difference. Output signals from the differential amplifiers 102, 104 can be applied to the microcontroller 65 integrated into the circuit board 64, and the microcontroller 65 can transmit the measured pressure data to a device external to the patient. If desired, a fully compensated Wheatstone bridge circuit can also be used to increase the sensitivity and accuracy of the pressure sensor 62. In a fully compensated bridge circuit, four strain gauges are attached to the surface of diaphragm rather than only two strain gauges.

Figure 7:
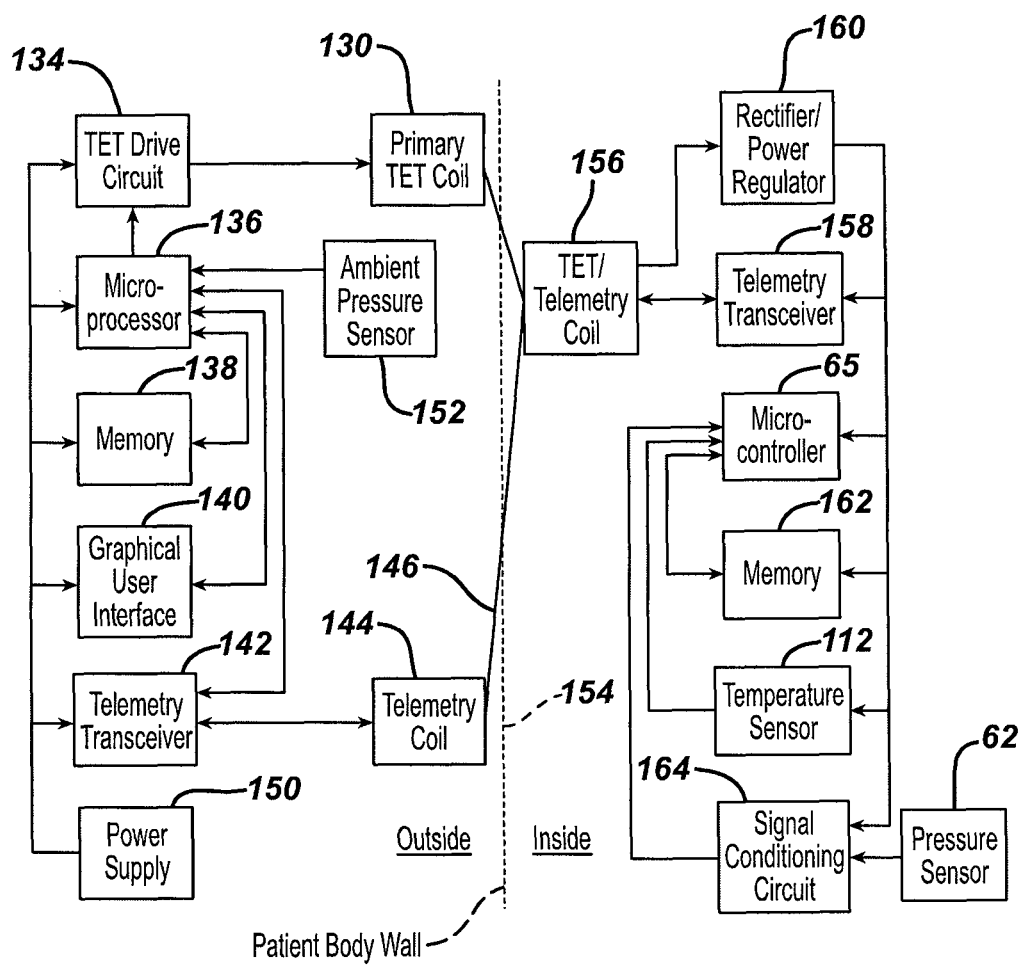
FIG. 7 is a block diagram showing an embodiment of internal and external components of the food intake restriction device of FIG. 1A.

FIG. 7 illustrates one embodiment of components included in the internal and external portions 10a, 10b. As shown in FIG. 7, the external portion 10b includes a primary TET coil 130 for transmitting a power signal to the internal portion 10a. A telemetry coil 144 is also included for transmitting data signals to the internal portion 10a. The primary TET coil 130 and the telemetry coil 144 combine to form an external antenna, e.g., the reading device 70. The external portion 10b, e.g., disposed in the control box 90, can include a TET drive circuit 134 for controlling the application of power to the primary TET coil 130. The TET drive circuit 134 is controlled by a microprocessor 136 having an associated memory 138. A graphical user interface 140 is connected to the microprocessor 136 for inputting patient information, displaying data and physician instructions, and/or printing data and physician instructions. Through the user interface 140, a user such as the patient or a clinician can transmit an adjustment request to the physician and can also enter reasons for the request. Additionally, the user interface 140 can enable the patient to read and respond to instructions from the physician and/or pressure measurement alerts.

The external portion 10b can also include a primary telemetry transceiver 142 for transmitting interrogation commands to and receiving response data, including sensed pressure data, from the implanted microcontroller 65. The primary transceiver 142 is electrically connected to the microprocessor 136 for inputting and receiving command and data signals. The primary transceiver 142 drives the telemetry coil 144 to resonate at a selected RF communication frequency. The resonating circuit can generate a downlink alternating magnetic field 146 that transmits command data to the microcontroller 65. Alternatively, the transceiver 142 can receive telemetry signals transmitted from a secondary TET/telemetry coil 156 ("the internal antenna") in the internal portion 10a. The received data can be stored in the memory 138 associated with the microprocessor 136. A power supply 150 can supply energy to the control box 90 in order to power element(s) in the internal portion 10a. An ambient pressure sensor 152 is connected to microprocessor 136. The microprocessor 136 can use a signal from the ambient pressure sensor 152 to adjust the received pressure measurements for variations in atmospheric pressure due to, for example, variations in barometric conditions or altitude, in order to increase the accuracy of pressure measurements.

FIG. 7 also illustrates components of the internal portion 10a, which in this embodiment are included in the sensor housing 60 (e.g., on the circuit board 64). As shown in FIG. 7, the secondary TET/telemetry coil 156 receives the power/communication signal from the external antenna. The secondary coil 156 forms a tuned tank circuit that is inductively coupled with either the primary TET coil 130 to power the implant or the primary telemetry coil 144 to receive and transmit data. A telemetry transceiver 158 controls data exchange with the secondary coil 156. Additionally, the internal portion 10a includes a rectifier/power regulator 160, the microcontroller 65, a memory 162 associated with the microcontroller 65, a temperature sensor 112, the pressure sensor 62, and a signal conditioning circuit 164. The implanted components can transmit pressure measurements (with or without adjustments due to temperature, etc.) from the sensor 62 to the control box 90 via the external antenna (the primary TET coil 130 and the telemetry coil 144). Pressure measurements can be stored in the memory 138, adjusted for ambient pressure, shown on a display on the control box 90, and/or transmitted, possibly in real time, to a remote monitoring station at a location remote from the patient.

As indicated above, the presently disclosed system can be configured in various manners so as to allow the implantable system to be powered by and/or communicate with an external reader. In an exemplary embodiment, the system can include an implantable antenna 156 which is configured to readily and predictably align with some external reference point (e.g., the external reader 70) in response to some force. For example, the antenna 156 can be configured so as to align with an external reader 70 in response to a magnetic force or an electromagnetic force being applied to a magnetic member in communication with the antenna 156. Also, the antenna 156 can be configured to align with the external reader 70 in response to a gravitational force being applied to the antenna 156. For example, the antenna 156 can be configured so as to adopt a known orientation when the patient assumes a certain position (e.g., standing). In short, the presently disclosed system can include any mechanism and/or configuration for easily and reliably aligning an implantable antenna 156 with the external reader 70 or some other external reference point.

Figure 8:
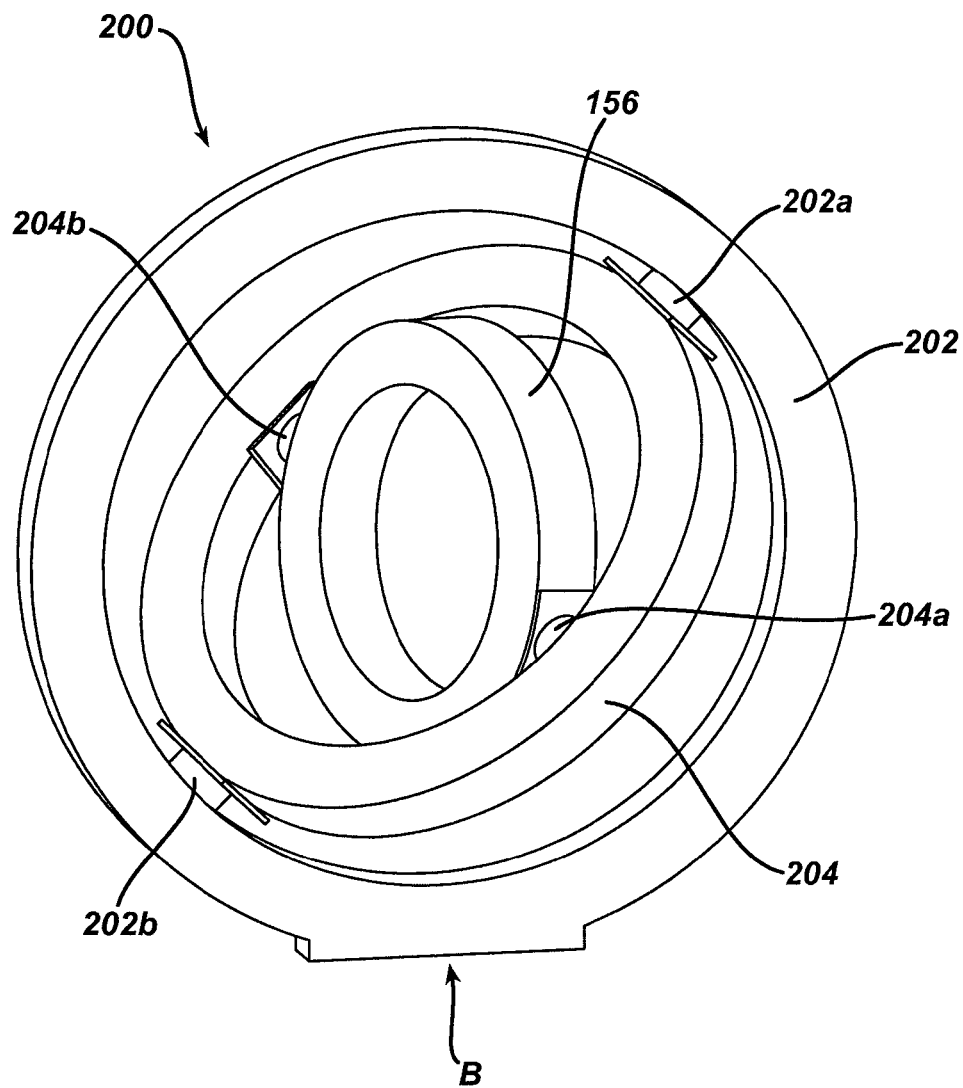
FIG. 8 is a representation of an implantable antenna coupled to a gimbal element thereby allowing the antenna to freely move relative to at least a first and second axis.

FIG. 8 provides an exemplary embodiment of a system having an implantable antenna 156 capable of readily and predictably aligning with an external device or reference point. As will be apparent to those skilled in the art, the internal antenna 156 can be any type, shape, and/or size of antenna capable of coupling with the external primary TET coil 130 and/or transmitting/receiving data to/from the external telemetry coil 144. For example, as shown in FIG. 8, the antenna 156 can be substantially ring-shaped. As further shown, in this embodiment the antenna 156 can be disposed within the system such that the antenna 156 can freely move and/or rotate independent of any movement of the patient. While such free movement can be provided in various manners, in an exemplary embodiment the antenna 156 can be coupled to a gimbal element 200 capable of allowing the antenna 156 to freely move and/or float independent of a patient's movement. More specifically, the gimbal element 200 can include an outer ring 202 having a first diameter wherein some portion of the outer ring 200 (e.g., a base portion (B)) can be secured, e.g., to the sensor housing 60. The outer ring 200 serves as a housing and it can have rotatably coupled thereto an inner ring 204 having a second diameter. As shown, the diameter of the inner ring 204 can be smaller than the diameter of the outer ring 202. Thus, the inner ring 204 can be coupled to the outer ring 202 at a first engagement point 202a and a second engagement point 202b such that the inner ring 204 can rotate along an axis extending between these engagement points 202a, 202b. Further, the antenna 156 can be similarly coupled at first and second engagement points 204a, 204b within the inner ring 204 such that the antenna 156 can rotate along a second axis extending between these engagement points 204a, 204b. Thus, in such an embodiment, the antenna 156 can be free to rotate about the first axis extending between the first set of engagement points 202a, 202b and also free to rotate relative to a second axis extending between the second set of engagement points 204a, 204b wherein the first axis is substantially orthogonal to the second axis. Those skilled in the art will appreciate that various other gimbal or gimbal-like elements can be utilized to provide various additional or alternative axes of rotation.

In the embodiment of FIG. 8, the antenna 156 can be manipulated relative to the inner 204 and outer ring 202 in various manners. For example, the antenna 156 can be shaped, configured, and/or have a certain weight so as to bias the antenna 156 in a certain position or orientation relative to an external device or reference point. For example, the antenna can be fabricated such that the antenna is always oriented in a desired position (e.g., vertically as shown in FIG. 8 or horizontally) independent of the patient's movement or position. In other embodiments, the antenna 156 can be fabricated so as to be oriented in a particular direction (e.g., horizontally or vertically) when the patient is in a certain position (e.g., standing). In another embodiment, the antenna 156 can be in communication with (e.g., coupled to) at least one magnetic element. Thus, as a magnetic force or an electromagnetic force is supplied to the antenna 156, the antenna 156 can rotate about the first and/or second axis so as to align the antenna 156 with the desired external device (e.g., the external reader 70). Another embodiment is to enclose the antenna assembly in a fluid-filled chamber and have at least a portion of one element of the antenna assembly comprised of a more buoyant material than the rest of the assembly. In such a configuration, the antenna can rotate about the first and/or second axis so as to align the antenna with the desired external device. Those skilled in the art will appreciate or recognize various other manners and/or mechanisms for rotating the antenna along the first axis and/or second axis so as to orient the antenna with the desired external reference point.

Figure 9:
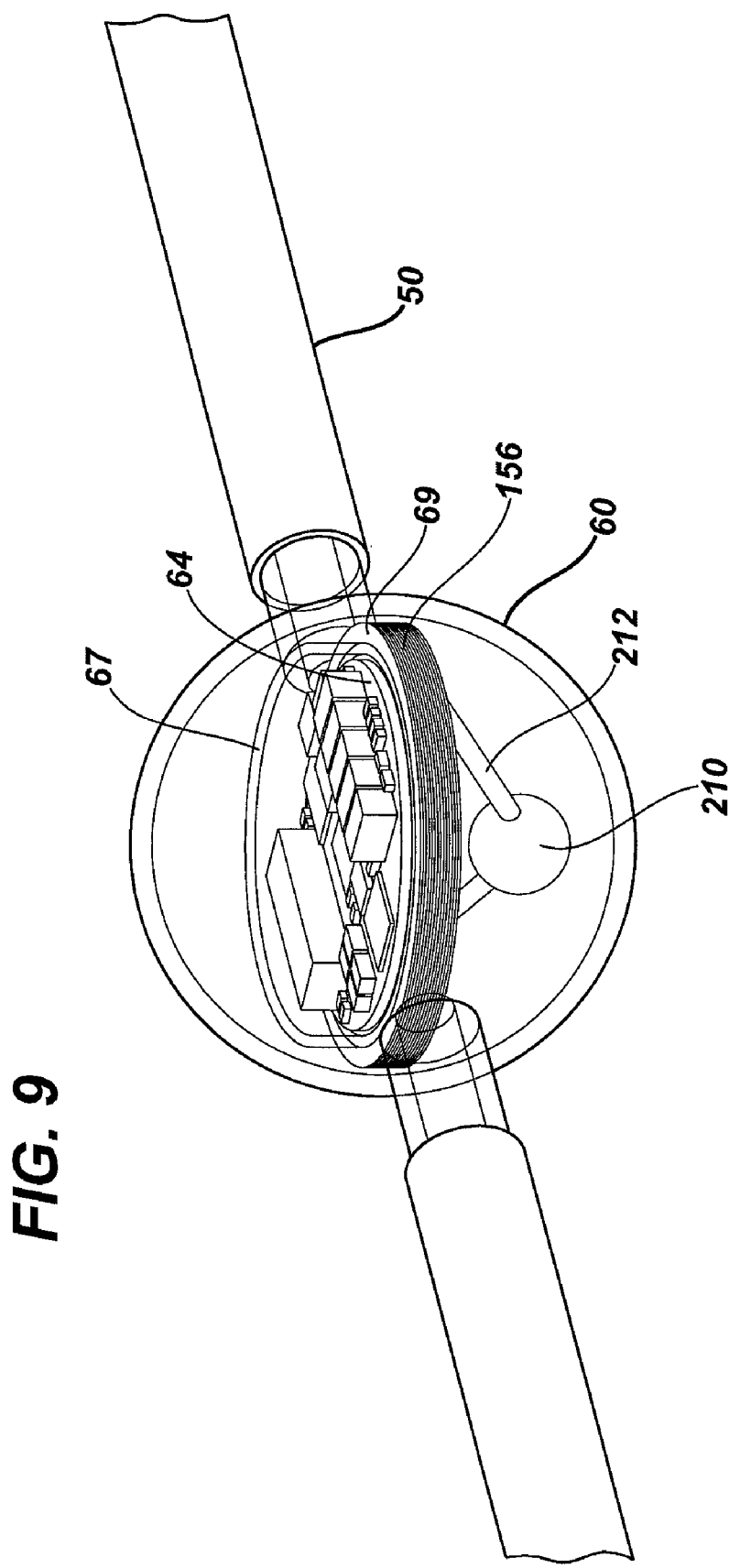
FIG. 9 is a representation of an implantable antenna coupled to a weight thereby allowing the antenna to assume a known orientation in response to a known gravitational force.

In other embodiments, the implantable antenna can be configured so as to adopt a known orientation in response to a gravitational force. For example, in such an embodiment the orientation of the antenna 156 can be predictably manipulated based on the orientation or posture of the patient (e.g., supine, upright, etc.). As will be appreciated by those skilled in the art, the antenna 156 can be configured in various manners so as to predictably align with an external reference point in response to such a gravitational force. For example, as shown in the exemplary embodiment of FIG. 9, the antenna 156 (again shown as a ring-shaped antenna) can be disposed in a substantially circular housing 70 that is disposed, for example, in a catheter 50 (FIGS. 1A, 1B) such that it is suspended in fluid passing through the system. In such an embodiment, various components of the sensor and/or internal electronics can be enclosed and hermetically sealed in an encapsulation capsule 67 so as to prevent contact with fluid passing therethrough. Further, the antenna 156 (which can be coiled around a floating support ring 69) can be coupled to a weight 210 (e.g., via any number of struts 212). One skilled in the art will appreciate that the shape, dimensions, properties, etc. of the weight 210 can be selected and optimized to provide the desired alignment. In this exemplary embodiment, the weight 210 can be positioned (e.g., suspended) below and substantially along a center line extending through the middle of the antenna 156 thereby allowing the gravitational force to be evenly distributed across the antenna 156. Thus, in this example, as a patient is in a standing position, the antenna 156 can be oriented in a substantially upward facing direction (i.e., horizontal, as shown in FIG. 9) thereby providing a predictable and easily reproducible result. In other embodiments, the antenna 156 can be mounted on or along a perimeter of the circuit board 64 (FIGS. 1A, 1B, and 5) such that the weighted side of the board 64 will always be pointing in a downward direction. As will be apparent to those skilled in the art, virtually any type or configuration of weight can be coupled to virtually any type or configuration of antenna in virtually any manner so as to enable the antenna to predictably align itself when subjected to a known gravitational field. Further, the geometry of the antenna may be such that the antenna is heavier in one location, thus acting as the weight.

Figure 10A:
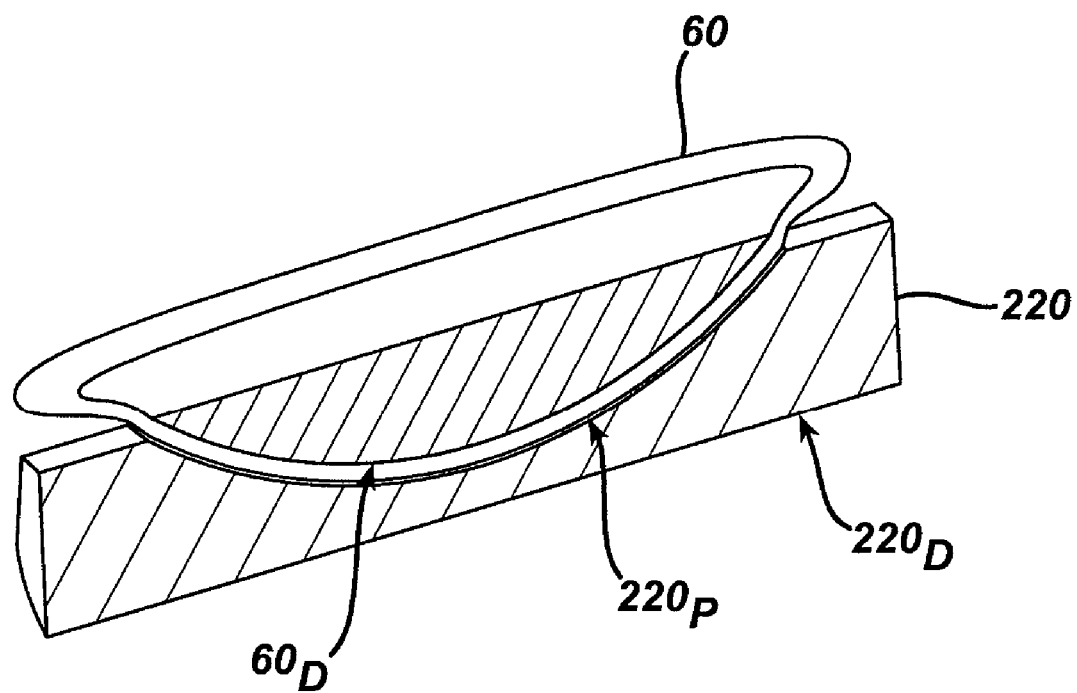
FIG. 10A is a cross-sectional representation of an embodiment of a housing movably coupled to a base.

In yet another embodiment, the antenna 156 can be disposed in a known orientation within or with respect to a housing 60 (i.e., statically mounted thereto) which can be pivotally mounted on a base housing configured to be secured to a desired anatomical location. Thus, following implantation, the housing 60 (and therefore the antenna 156) can be readily manipulated relative to the base housing so as to align the antenna 156 with a known external reference point (e.g. an external reader 70). Those skilled in the art will appreciate that the housing 60 can be mated to the base housing in various manners so as to provide such pivotable movement. For example, as shown in FIG. 10A, the housing 60 can include a distal or bottom surface $60_D$. Further, the housing 60 can be pivotally coupled to a base housing 220 having a proximal surface $220_P$ that is configured to couple to the housing 60 and a distal surface $220_D$ that is configured to rest on and/or anchor to a desired anatomical location (e.g., the fascia). The distal surface $220_D$ of the base housing 220 can be anchored to tissue in a variety of ways. For example, the base housing 220 can include one or more suture-receiving members (not shown) configured to receive a suture for anchoring the base housing 220 to tissue, and/or the base housing 220 can include one or more anchors (not shown) configured to be deployed into tissue. One skilled in the art will appreciate that the any technique can be used to anchor the base housing 220 in tissue.

Figure 10B:
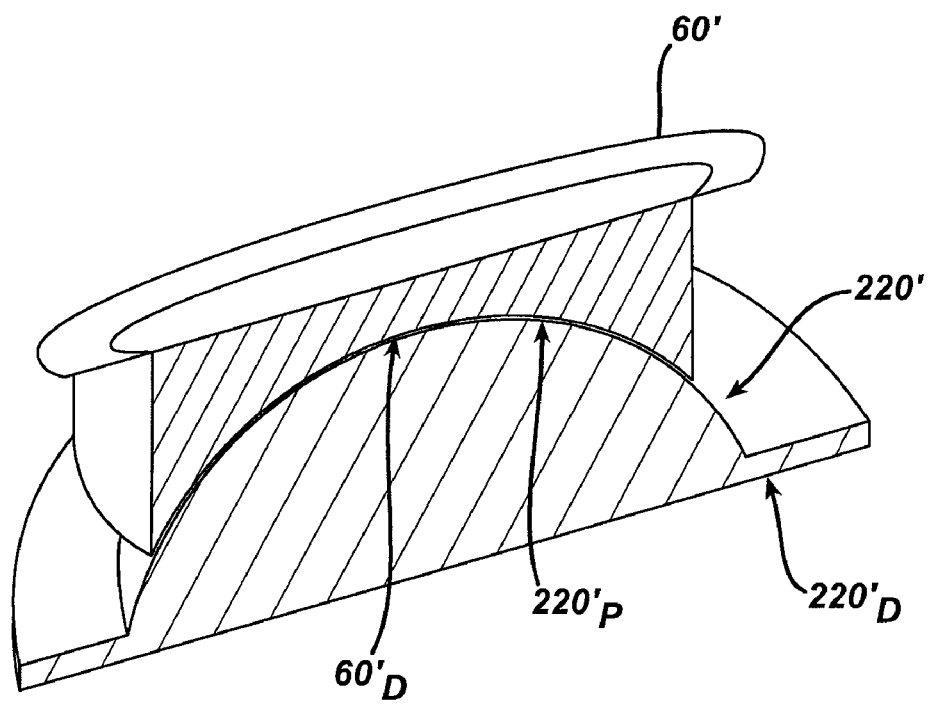
FIG. 10B is a cross-sectional representation of an alternative embodiment of a housing movably coupled to a base.

In order to facilitate reorientation of the internal antenna, the distal surface $60_D$ of the housing 60 and the proximal surface $220_P$ of the base housing 220 can be configured to move relative to one another. In one exemplary embodiment, the distal surface $60_D$ of the housing 60 and the proximal surface $220_P$ of the base housing 220 are configured to move relative to one another, for example, using a ball and socket configuration. In one embodiment, shown in FIG. 10A, the distal surface $60_D$ of the housing 60 is convex and is configured to be received within a corresponding concave proximal surface $220_P$ of the base housing 220. This allows the housing 60 to move relative to the base housing 220 to reorient the housing 60 when the base housing 220 is positioned on and/or anchored in tissue. In another embodiment, shown in FIG. 10B, the distal surface 60'$_D$ of the housing 60' can include a concave cavity and it can be configured to receive a corresponding convex surface formed on the proximal surface 220'$_P$ of the base housing 220'. One skilled in the art will appreciate that any configuration of the housing 60 and the base housing 220 can be used as long as the housing 60 and the base housing 220 can move relative to one another to allow reorientation of the antenna.

Figure 10C:
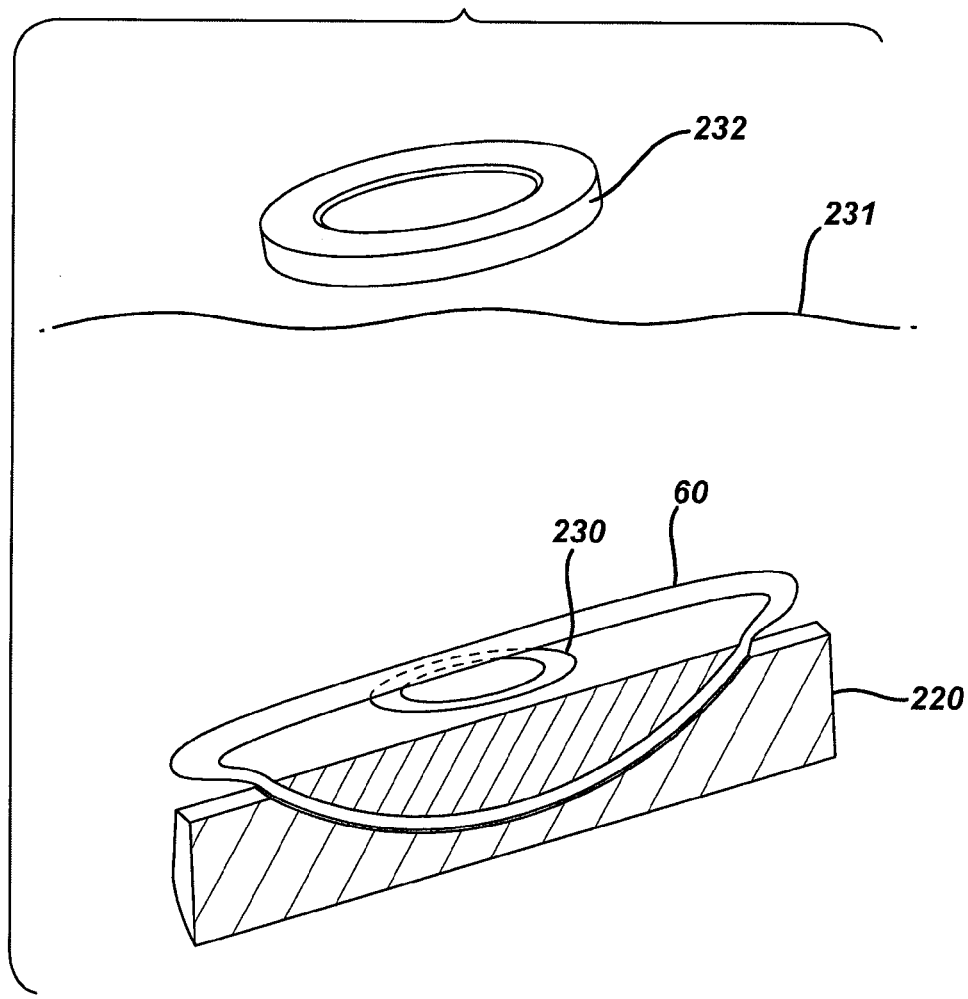
FIG. 10C is a cross-sectional representation of the housing of FIG. 10A wherein the housing further includes a magnetic element.

In another embodiment, as shown in FIG. 10C, the internal antenna 156 and/or the housing 60 can include a magnetic element 230 coupled thereto for facilitating reorientation of the antenna 156. The magnetic element 230 can have a variety of configurations and more than one magnetic element can be used. In one example, the magnetic element 230 can be in the form of a cylindrical magnet with an opening therethrough. Those skilled in the art will appreciate that the magnet 230 can be disposed with the housing 60 and/or coupled to the housing 60 in virtually any manner known in the art. For example, the magnet 230 (or a number of magnet elements) can be coupled to an outer portion of the housing 60, coupled to an inner portion of the housing 60, formed within the housing 60, etc. In use, as shown in FIG. 10C, the magnetic member 230 can be used in conjunction with an external magnet or electromagnet 232 that is placed against a skin surface 231. The external magnet 232 can be used to apply a force to the magnetic element 230 coupled to the housing 60 to align the external magnet 232 and the magnetic element 230. This can cause the housing 60 to pivot relative to the base housing 220 thereby reorienting the housing 60 so that the internal antenna is directed towards the skin surface 231.

Additionally, various embodiments of a method for transcutaneously communicating with an implantable restriction system are provided herein. In general, the presently disclosed embodiments allow a user to readily and predictably align an implantable antenna with an external device (e.g., an external antenna or reader). Once properly aligned, the implantable antenna can easily communicate with an external antenna thereby allowing the implantable system to be powered and/or various system and/or physiological parameters (e.g., pressure readings) to be transmitted/received from the implantable antenna to/from some external antenna or reader.

More specifically, in an exemplary embodiment, the method includes implanting a restriction system within a patient wherein the system includes a device effective to form a restriction in a pathway and an antenna effective to communicate with an external device to receive and transmit at least one of energy and data. The method also includes enabling the antenna to be movable with respect to at least a portion of a housing such that the antenna can align with the external device for communicating therewith. As described above, various manners or mechanisms can be utilized to move and/or manipulate the implantable antenna. For example, the antenna can align with the external device in a desired orientation in response to at least one of manual manipulation, a magnetic force, an electromagnetic force, and a gravitational force.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An implantable restriction system, comprising:
  an implantable restriction device configured to form a restriction in a pathway;
  an implantable housing; and
  an implantable antenna movably mounted on the housing such that the antenna can align with an external device for communicating therewith,
  wherein the housing is at least a portion of a gimbal element such that the antenna is free to rotate about a first axis and the antenna is also free to rotate about a second axis, the first axis being substantially orthogonal to the second axis.

2. The system of claim 1, further comprising at least one magnetic element coupled to the antenna.

3. The system of claim 2, wherein the at least one magnetic element is configured to align with an external magnetic member.

4. The system of claim 1, wherein the antenna is movable in response to at least one of manual manipulation, a magnetic force, an electromagnetic force, a gravitational force, and a buoyant force.

5. The system of claim 1, further comprising an implantable sensor configured to measure at least one of an operational value of a system parameter and a value of a physiological parameter, wherein the antenna is effective to communicate the operational value or the physiological value to the external device.

6. The system of claim 5, wherein the antenna is disposed on a sensor housing that is movably mounted to a base housing that is configured to engage an anatomical location.

7. The system of claim 6, wherein the antenna is statically mounted upon the sensor housing.

8. The system of claim 1, wherein the antenna is effective to communicate with the external device to transcutaneously deliver energy to power the implantable restriction device.

9. An implantable restriction system, comprising:
  an implantable restriction device configured to form a restriction in a pathway;
  an implantable housing;
  an implantable antenna movably mounted on the housing such that the antenna can align with an external device for communicating therewith; and
  an implantable sensor configured to measure at least one of an operational value of a system parameter and a value of a physiological parameter, wherein the antenna is effective to communicate the operational value or the physiological value to the external device,
  wherein the antenna is disposed on a sensor housing that is movably mounted to a base housing that is configured to engage an anatomical location, and wherein the sensor housing is movably mounted to the base housing by way of a ball and socket joint.

10. The system of claim 9, further comprising at least one magnetic element coupled to the antenna.

11. The system of claim 10, wherein the at least one magnetic element is configured to align with an external magnetic member.

12. The system of claim 9, wherein the antenna is movable in response to at least one of manual manipulation, a magnetic force, an electromagnetic force, a gravitational force, and a buoyant force.

13. The system of claim 9, wherein the antenna is effective to communicate with the external device to transcutaneously deliver energy to power the implantable restriction device.

14. An implantable restriction system, comprising:
an implantable gastric restriction device configured to form a restriction in a patient;
an implantable sensor configured to measure at least one of a value of a system parameter and a physiological parameter; and
an implantable antenna in communication with the implantable sensor, the implantable antenna configured to communicate with an external device and to be capable of achieving an effective orientation to enable the antenna to communicate with the external device,
wherein the implantable antenna is mounted on a housing wherein the housing is at least a portion of a gimbal element such that the antenna is free to rotate about a first axis and the antenna is also free to rotate about a second axis, the first axis being substantially orthogonal to the second axis.

15. The system of claim 14, wherein the antenna is movable to the effective orientation in response to at least one of manual manipulation, a magnetic force, an electromagnetic force, a gravitational force, and a buoyant force.

16. A method for transcutaneously communicating with an implantable restriction system, comprising:
implanting a restriction system within a patient such that the system includes a device effective to form a restriction in a pathway and an antenna effective to communicate with an external device to receive and transmit at least one of energy and data; and
enabling the antenna to be movable with respect to at least a portion of a housing such that the antenna can align with the external device for communicating therewith, wherein the housing is at least a portion of a gimbal element such that enabling the antenna comprises enabling the antenna to be free to rotate about a first axis and free to rotate about a second axis, the first axis being substantially orthogonal to the second axis.

17. The method of claim 16, wherein the antenna aligns with the external device in a desired orientation in response to at least one of manual manipulation, a magnetic force, an electromagnetic force, a gravitational force, and a buoyant force.

* * * * *